US012564321B2

(12) United States Patent
Hunter

(10) Patent No.: US 12,564,321 B2
(45) Date of Patent: Mar. 3, 2026

(54) METHOD TO MONITOR ACCOMMODATION STATE DURING VISUAL TESTING

(71) Applicant: Welch Allyn, Inc., Skaneateles Falls, NY (US)

(72) Inventor: Vivian Loomis Hunter, Auburn, NY (US)

(73) Assignee: Welch Allyn, Inc., Skaneateles, NY (US)

( * ) Notice: Subject to any disclaimer, the term of this patent is extended or adjusted under 35 U.S.C. 154(b) by 497 days.

(21) Appl. No.: 18/094,909

(22) Filed: Jan. 9, 2023

(65) Prior Publication Data

US 2023/0218163 A1 Jul. 13, 2023

Related U.S. Application Data

(60) Provisional application No. 63/298,427, filed on Jan. 11, 2022.

(51) Int. Cl.
| | |
|---|---|
| *A61B 3/103* | (2006.01) |
| *A61B 3/00* | (2006.01) |
| *A61B 3/11* | (2006.01) |

(52) U.S. Cl.
CPC ............ *A61B 3/103* (2013.01); *A61B 3/0025* (2013.01); *A61B 3/112* (2013.01)

(58) Field of Classification Search
CPC ....... A61B 3/112; A61B 3/103; A61B 3/0025; A61B 3/032; A61B 3/00; A61B 3/11; A61B 3/10–165

USPC .................................................. 351/205–221
See application file for complete search history.

(56) References Cited

U.S. PATENT DOCUMENTS

| | | | |
|---|---|---|---|
| 7,290,879 B2 | 11/2007 | Nagata et al. | |
| 7,344,247 B2 | 3/2008 | Isogai et al. | |
| 8,113,655 B1 | 2/2012 | Tyrin et al. | |
| 8,591,027 B2 | 11/2013 | Su et al. | |
| 8,851,670 B2 | 10/2014 | Dai et al. | |
| 10,827,918 B1 * | 11/2020 | Nuriel ...................... | A61B 3/08 |
| 11,156,835 B2 | 10/2021 | Samec et al. | |
| 2006/0187412 A1 | 8/2006 | Nagata et al. | |
| 2015/0374233 A1 | 12/2015 | Zhang et al. | |
| 2017/0293145 A1 * | 10/2017 | Miller ...................... | G06F 1/163 |
| 2019/0125183 A1 * | 5/2019 | Lane .................... | A61B 3/0025 |
| 2019/0148017 A1 * | 5/2019 | Seriani ................... | G16H 50/20 |
| | | | 705/2 |
| 2021/0290053 A1 | 9/2021 | Tran et al. | |

(Continued)

FOREIGN PATENT DOCUMENTS

EP        3888525        10/2021

*Primary Examiner* — Marin Pichler
*Assistant Examiner* — Kuei-Jen L Edenfield
(74) *Attorney, Agent, or Firm* — Lee & Hayes, P.C.

(57) ABSTRACT

A vision screening device displays visual stimuli and captures image(s) of the eye while the visual stimuli is changing over a period of time. The vision screening device uses the images to determine and monitor refractive error, ambient light level(s), pupil size, and gaze angle as the visual stimuli changes over the time period. Based on the refractive error, a determination of hyperopia and/or presbyopia is made. Based on the gaze angle and/or the pupil size, a confidence metric is determined. Based on the confidence metric and/or the determination, a recommendation for the patient is generated and displayed.

20 Claims, 6 Drawing Sheets

(56) References Cited

U.S. PATENT DOCUMENTS

| 2022/0192483 A1* | 6/2022 | Lee | ...................... | A61B 3/0041 |
| 2023/0200639 A1* | 6/2023 | Yehezkel | ............. | A61B 3/0041 |
| | | | | 351/222 |

* cited by examiner

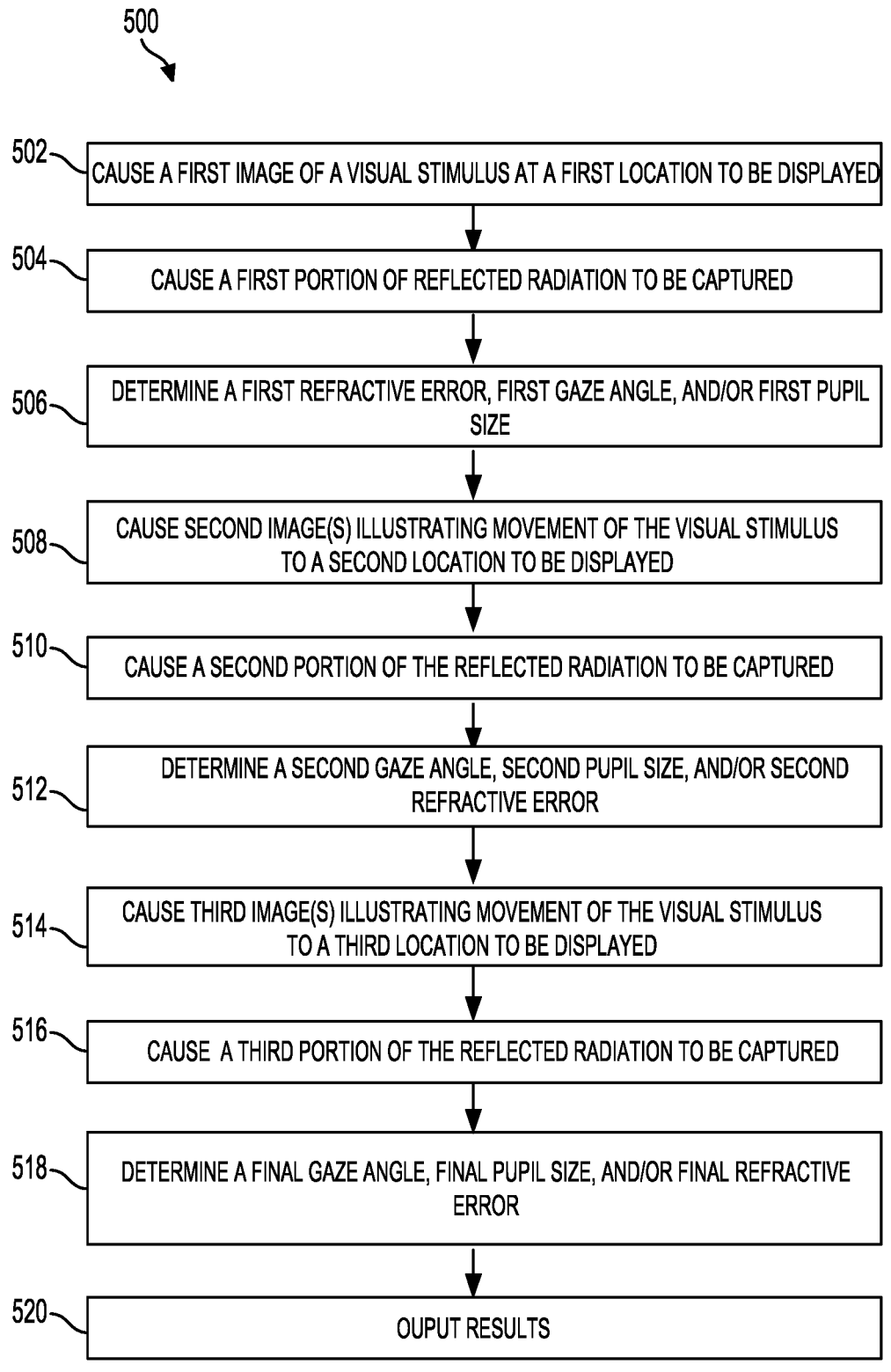

500

502 — CAUSE A FIRST IMAGE OF A VISUAL STIMULUS AT A FIRST LOCATION TO BE DISPLAYED

504 — CAUSE A FIRST PORTION OF REFLECTED RADIATION TO BE CAPTURED

506 — DETERMINE A FIRST REFRACTIVE ERROR, FIRST GAZE ANGLE, AND/OR FIRST PUPIL SIZE

508 — CAUSE SECOND IMAGE(S) ILLUSTRATING MOVEMENT OF THE VISUAL STIMULUS TO A SECOND LOCATION TO BE DISPLAYED

510 — CAUSE A SECOND PORTION OF THE REFLECTED RADIATION TO BE CAPTURED

512 — DETERMINE A SECOND GAZE ANGLE, SECOND PUPIL SIZE, AND/OR SECOND REFRACTIVE ERROR

514 — CAUSE THIRD IMAGE(S) ILLUSTRATING MOVEMENT OF THE VISUAL STIMULUS TO A THIRD LOCATION TO BE DISPLAYED

516 — CAUSE A THIRD PORTION OF THE REFLECTED RADIATION TO BE CAPTURED

518 — DETERMINE A FINAL GAZE ANGLE, FINAL PUPIL SIZE, AND/OR FINAL REFRACTIVE ERROR

520 — OUPUT RESULTS

*FIG. 5*

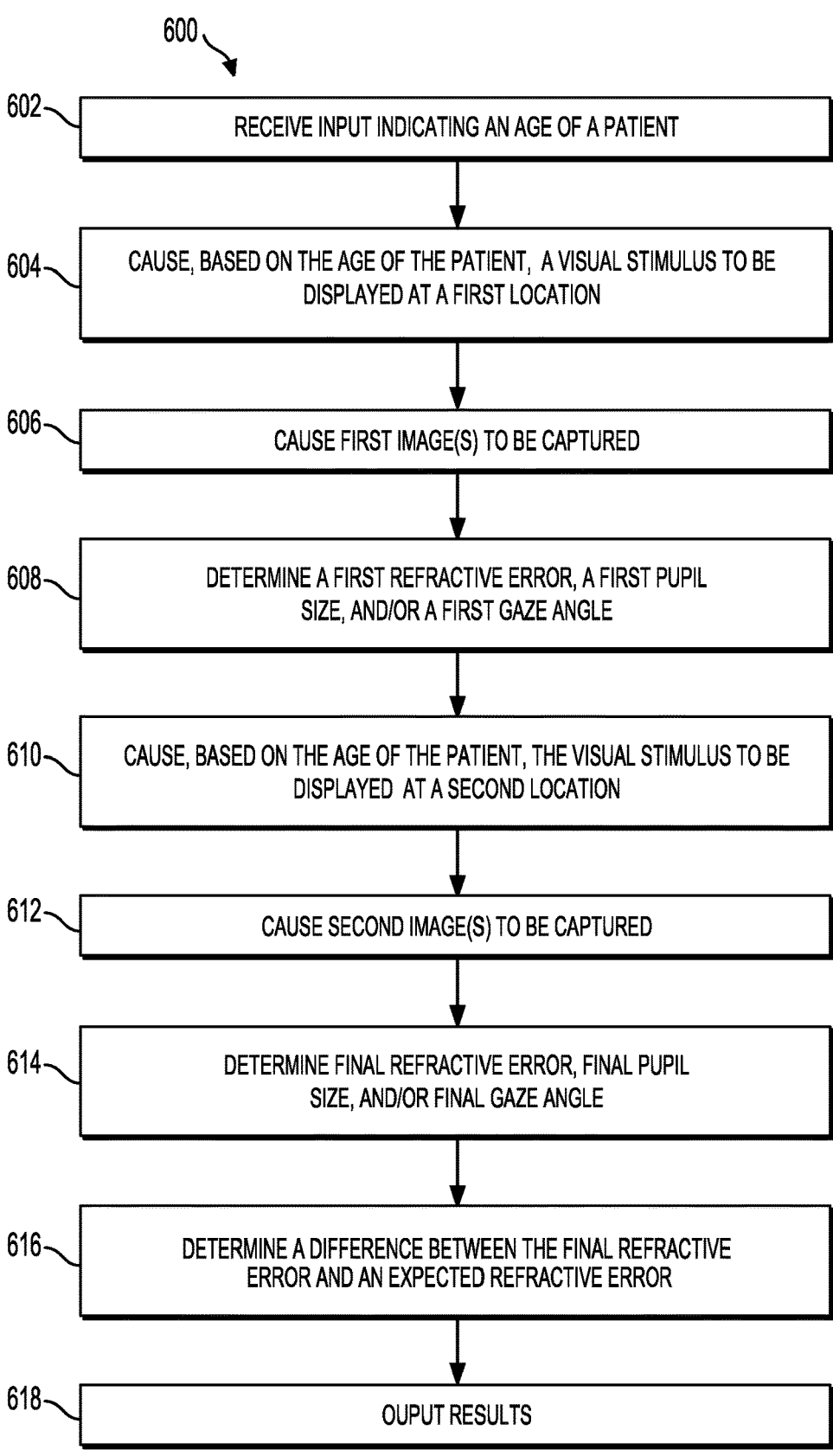

600

602 — RECEIVE INPUT INDICATING AN AGE OF A PATIENT

604 — CAUSE, BASED ON THE AGE OF THE PATIENT, A VISUAL STIMULUS TO BE DISPLAYED AT A FIRST LOCATION

606 — CAUSE FIRST IMAGE(S) TO BE CAPTURED

608 — DETERMINE A FIRST REFRACTIVE ERROR, A FIRST PUPIL SIZE, AND/OR A FIRST GAZE ANGLE

610 — CAUSE, BASED ON THE AGE OF THE PATIENT, THE VISUAL STIMULUS TO BE DISPLAYED AT A SECOND LOCATION

612 — CAUSE SECOND IMAGE(S) TO BE CAPTURED

614 — DETERMINE FINAL REFRACTIVE ERROR, FINAL PUPIL SIZE, AND/OR FINAL GAZE ANGLE

616 — DETERMINE A DIFFERENCE BETWEEN THE FINAL REFRACTIVE ERROR AND AN EXPECTED REFRACTIVE ERROR

618 — OUPUT RESULTS

*FIG. 6*

METHOD TO MONITOR ACCOMMODATION STATE DURING VISUAL TESTING

CROSS REFERENCE TO RELATED APPLICATION

This application is a Nonprovisional of, and claims priority to, U.S. Provisional Patent Application No. 63/298,427, filed Jan. 11, 2022, the entire disclosure of which is incorporated herein by reference.

TECHNICAL FIELD

The present application relates to systems and methods for measuring an accommodation state with a vision screening device during visual acuity testing.

BACKGROUND

Visual acuity is a person's ability to identify characters at a particular distance. "Normal" visual acuity is generally determined during a vision screening exam and is generally defined as being 20/20 vision. However, various conditions impact whether a person has "Normal" vision, such as whether the person has myopia (e.g., is nearsighted), hyperopia (e.g., is farsighted), or presbyopia (e.g., farsightedness usually related to a patient's age, resulting in patient not being able to focus on near objects).

Visual screening in children and adults typically includes one or more tests to determine various deficiencies associated with the patient's eyes. Such vision tests may include, for example, refractive error tests, convergence tests, accommodation tests, visual acuity tests, and the like. Conventional vision tests may include the use of an ophthalmic testing device called a phoropter, which uses different lenses for refraction of the eye to measure an individual's refractive error, and in some cases may be used to determine an eyeglass prescription. Conventional phoropters rely upon a patient's feedback on various trial lenses, and in some cases this technique for relying upon feedback from the patient can lead to inaccurate results, such as with small children who may have difficulty communicating during an eye exam.

Moreover, a person's determined refractive error may not be accurate. For instance, hyperopic patients, especially children, may appear to have a "normal" refractive error e.g., a refractive error of zero). This occurs due to the ability of the hyperopic patient's eye being able to accommodate, such that their actual resting refractive state is disguised, rendering the eye examination essentially useless as the patient's eye adapts and nullifies the effect of the resting refractive rate, such that the patient's refractive error appears to be zero. Accordingly, hyperopia is difficult to measure and normal eye exams can result in refractive error testing being inaccurate and patients with hyperopia not being identified or treated. Obtaining accurate refractive error testing for patients with hyperopia is difficult and requires the patient to induce far vision (e.g., focus on an object in the distance), such that we can accurately record their refractive state and not allow their eye to accommodate.

Current techniques for measuring hyperopia include using non-portable refractometers, where a patient looks through the refractometer and tries to focus on a back wall or object in the distance. Alternatively, physicians may give patients eye drops that prevent the lens of the eye from accommodating. However, these techniques have variable effectiveness, are time consuming, and require additional equipment, which can be costly.

In some instances, a large number of people undergo visual acuity screening in a given time frame. For example, a group of kindergarten students at a public school may be screened during a class period. Usually, each kindergarten student waits their turn to be screened, then each student reads up to 30 characters for each eye. This is a time-consuming undertaking, which can test the limits of the children's patience. Moreover, the use of eye drops in this scenario is impractical and invasive. In some examples, a hand-held device is used during the vision screening exams to determine visual acuity, such as via eccentric photorefraction. While current hand-held devices may accurately determine refractive error for the purposes of identifying myopia, current hand-held devices do not provide means for accurately determining whether a patient has hyperopia and/or presbyopia by monitoring the patient's accommodation state during a visual acuity test. Accordingly, identifying hyperopia and/or presbyopia can be time consuming, costly (e.g., such as requiring additional equipment), invasive (e.g., by requiring eye drops), and inefficient (e.g., such as for groups).

SUMMARY in an example of the present disclosure, a system comprises a processing unit, a first display unit operatively connected to the processing unit, a second display unit operatively connected to the processing unit, a light sensor operatively connected to the processing unit, and non-transitory computer-readable media. The non-transitory computer-readable media can store instructions that, when executed by the processing unit, cause the processing unit to perform operations comprising: causing a first image including a visual stimulus to be displayed on the first display unit, the first display unit directing radiation to an eye of a patient, causing, a first portion of the radiation reflected from the eye to be captured by the light sensor and during display of the first image, and determining, based at least in part on the first portion of the radiation, a first refractive error, causing a plurality of second images including the visual stimulus to be displayed on the first display unit, the plurality of second images illustrating movement of the visual stimulus, from a first location on the first display unit to a second location on the first display unit, causing, during display of the plurality of second images, a second portion of the radiation reflected from the eye of the patient to be captured by the light sensor while the visual stimulus moves from the first location to the second location, determining, based at least in part on the second portion of the radiation, a second refractive error, and causing a recommendation to be displayed on the second display unit.

In yet another example of the present disclosure, a system comprises a processing unit, a first display unit operatively connected to the processing unit, a second display unit operatively connected to the processing unit, a light sensor operatively connected to the processing unit, and non-transitory computer-readable media. The non-transitory computer-readable media can store instructions that, when executed by the processing unit, cause the processing unit to perform operations comprising receiving an input via the second display unit indicating an age of a patient, causing, based on the age of the patient, a first image of a plurality of images to be displayed, the first image including a visual stimulus on the first display unit, the first display unit directing radiation to an eye of the patient, causing, by the light sensor, a first portion of radiation reflected from the eye of the patient to be captured, determining, based at least in part on the first portion of the radiation, a first refractive error, causing, based on the age of the patient, second images of the plurality of images to be displayed, the second images including the visual stimulus on the first display unit and illustrating movement of the visual stimulus from a first location on the first display unit to a second location on the first display unit, causing, by the light sensor, a second portion of the radiation reflected from the eye of the patient to be captured while the visual stimulus moves from the first location to the second location, determining, based at least in part on the second portion of the radiation, a second refractive error, and causing a recommendation to be displayed on the second display unit.

The details of one or more embodiments are set forth in the accompanying drawings and the description below. Other features, objects, and advantages of these embodiments will be apparent from the description, drawings, and claims.

DESCRIPTION OF THE FIGURES

The present invention may comprise one or more of the features recited in the appended claims and/or one or more of the following features or combinations thereof. Additionally, in this specification and drawings, features similar to or the same as features already described may be identified by reference characters or numerals which are the same as or similar to those previously used. Similar elements may be identified by a common reference character or numeral, with suffixes being used to refer to specific occurrences of the element

FIG. 5 illustrates a flow chart corresponding to an example method associated with the example vision screening device described herein.

FIG. 6 illustrates an additional flow chart corresponding to a further example method associated with the example vision screening device described herein.

DETAILED DESCRIPTION

Figure 1:
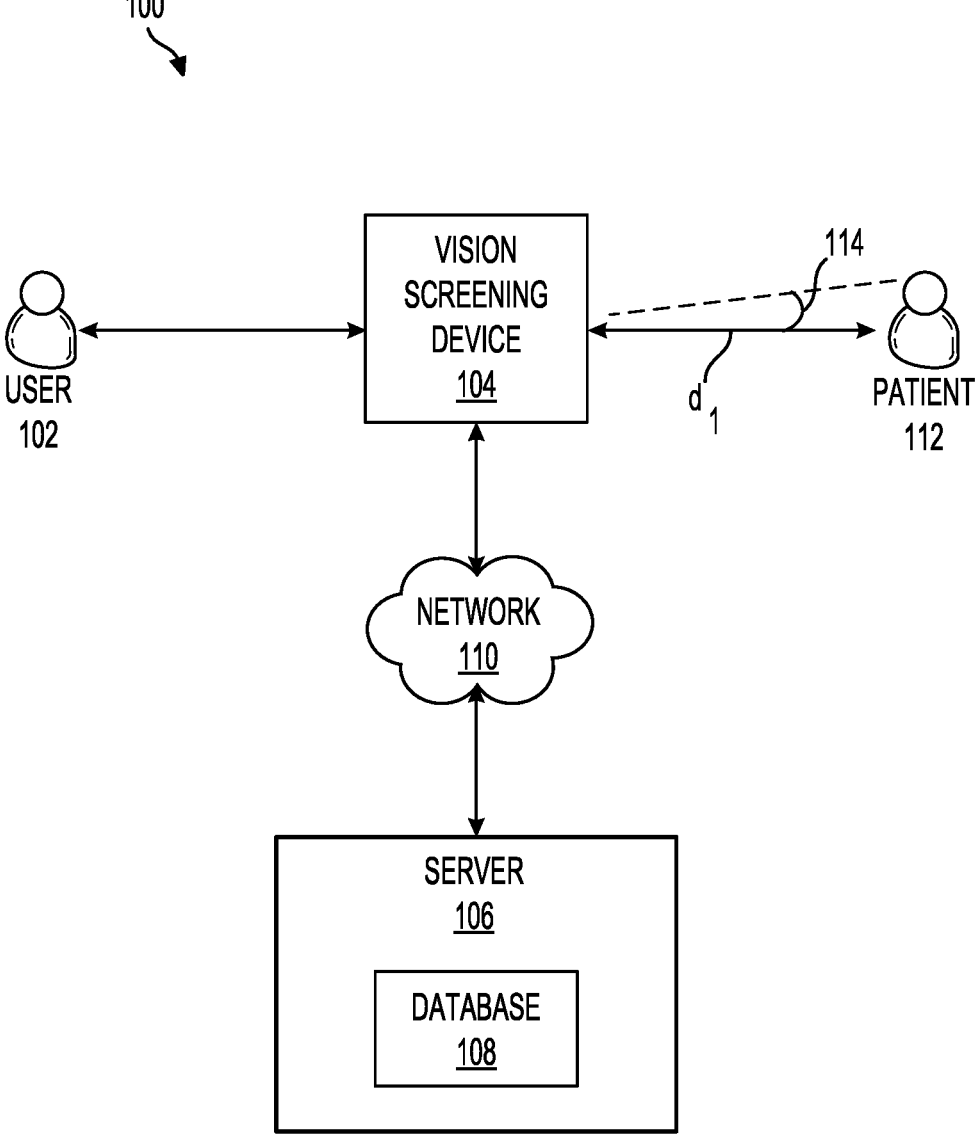
FIG. 1 shows a schematic block diagram of an example visual acuity screening environment.

FIG. 1 is a schematic block diagram of an example visual acuity screening environment 100. The example visual acuity screening environment 100 includes a user 102, vision screening device 104, server 106, database 108, and a patient 112. Vision screening device 104 and server 106 are in communication via network 110. In typical operation, user 102 operates vision screening device 104 to test a patient 112 (e.g., any evaluated person). Other embodiments can include more or fewer components. For example, in any of the embodiments described herein, one or more of the refractive error determinations, cornea curvature determinations, axial length determinations, and/or other determinations may be made by a processor or other controller of the vision screening device 104, such as processing unit 208 (FIG. 2) described in greater detail below. In some examples, such determinations may be made by the processor or controller of the vision screening device 104 alone or at least partly in conjunction with the server 106.

Vision screening device 104 is a portable device configured to perform a vision screening test on the patient 112. Although common environments include schools and portable or permanent medical clinics, because vision screening device 104 is portable, it can be used virtually anywhere the user 102 takes the vision screening device 104. A commercial embodiment of example vision screening device 200 is the Spot™ Vision Screener VS100 by Welch Allyn, Inc.® (Skaneateles Falls, NY). Other embodiments can include more or fewer components as those described herein.

Vision screening device 104 is capable of performing both refractive error testing, visual acuity testing, and facilitating vision screening testing. At a broad level, refractive error testing includes displaying stimuli, detecting pupils, acquiring images of the pupils, and analyzing pupil image data to generate refractive error results. As described in greater detail below, in some examples, vision screening testing includes determining a distance d1 of the patient 112 from the vision screening device 104, determining an angle (e.g., gaze angle) 114 of the vision screening device 104 relative to the patient 112, determining a refractive error for at least one eye of the patient 112, determining a pupil size of at least one eye of the patient, generating a recommendation and/or output for the patient 112, and/or displaying the recommendation and/or output. In some examples, vision screening testing further includes determining a confidence metric associated with the refractive error.

In some examples, vision screening device 104 communicates with server 106, such as via network 110. For instance, a processor of vision screening device 104 may determine the refractive error results based on the analysis of pupil image data as noted above. In some examples, refractive error results are determined based at least in part on demographics, sphere, cylinder, axis, pupillometry and/or other characteristics of the patient 112. In still further examples, refractive error results are determined based at least partly on the accommodation range, binocular gaze deviation, pupillary reaction to the "brightness" of the fixation target, and pre-existing eye or neurological conditions. Objective visual acuity data, such as optic kinetic nystagmus (OKN) data can also be used. In some instances, the server 106 may have access to one or more of these data, for example, by communicating with the database 108 and/or with an electronic health record/electronic medical record database via network 110. In such examples, the server 106 may provide such information to the processor of the vision screening device 104 such that the processor of the vision screening device 104 can determine the refractive error of the patient 112 based at least in part on such data. Additionally or alternatively, such information may be stored locally within a memory associated with and/or in communication with the vision screening device 104 (e.g., such as memory of the processing unit 208, described in greater detail below). The processor of the vision screening device 104 may transmit refractive error testing results to the server 106 via network 110. Server 106, alone or in combination with database 108, determines corresponding vision acuity data based on the refractive error data received from vision screening device 104. For instance, in some examples, the server may process and/or analyze images received by the vision screening device 104 and determine, based at least partly on the image(s), one or more of refractive error, pupil size, and/or gaze angle of the one or more eyes of a patient 112. In some examples, the server 106 analyzes the image(s) using image processing techniques (e.g., positional analysis, object detection, etc.) and/or machine learning mechanisms. In some examples, the server determines refractive error, a confidence metric, and/or a recommendation. In this example, the server 106 transmits the corresponding vision acuity data, refractive error, confidence metric, and/or recommendation to the processor of the vision screening device 104. The processor of the vision screening device 104 uses the corresponding acuity data to provide a vision screening test for the patient 112. In some examples, the server 106 determines corresponding vision acuity data associated with the patient 112 and transmits the corresponding vision acuity data to the processor of the vision screening device 104. In this example, the processor of the vision screening device 112 uses the vision acuity data to determine refractive error, confidence metric, and/or a recommendation for the patient 112. For instance, the server may utilize age, gaze angle, or other data included in the vision acuity data to make one or more of the determinations. As noted above, in some examples, the server may process and/or analyze images received by the vision screening device 104 and determine, based at least partly on the image(s), one or more of refractive error, pupil size, and/or gaze angle of the one or more eyes of a patient 112. In some examples, the server 106 may determine a refractive error, confidence metric, and/or recommendation for the patient 112 using machine learning mechanisms.

In alternative implementations, vision screening device 104 determines corresponding vision acuity data based on the refractive error data. In those implementations, vision screening device 104 may communicate with server 106 to check for updates to any correspondence data or algorithms but otherwise does not rely on server 106 and/or database 108 for determining refractive error or corresponding acuity data. Vision screening device 104 and methods of using vision screening device 104 are described in greater detail below. In some instances, vision screening device 104 can be in communication with user 102 specific devices, such as mobile phones, tablet computers, laptop computers, etc., to deliver or communicate results to those devices.

Server 106 communicates with vision screening device 104 to respond to queries, receive data, and communicate with database 108. Communication from vision screening device 104 occurs via network 110, where the communication can include requests for corresponding acuity data. Server 106 can act on these requests from vision screening device 104, determine one or more responses to those queries, and respond back to vision screening device 104. Server 106 accesses database 108 to complete transactions by a vision screening device 104. In some examples, server 106 includes one or more computing devices, such as computing device 202 described in greater detail below.

Database 108 comprises one or more database systems accessible by server 106 storing different types of information. In some examples, database 108 stores correlations and algorithms used to determine vision acuity data based on refractive error testing. In some examples, database 108 stores clinical data associated with one or more patient(s) 112. In some examples, database 108 resides on server 106. In other examples, database 108 resides on patient computing device(s) that are accessible by server 106 via a network 110.

Network 110 comprises any type of wireless network or other communication network known in the art. In some examples, the network 110 comprises a local area network ("LAN"), a WiFi direct network, wireless LAN ("WLAN"), a larger network such as a wide area network ("WAN"), cellular network connections, or a collection of networks, such as the Internet. Protocols for network communication, such as TCP/IP, 802.11a, b, g, n and/or ac, are used to implement the network 110. Although embodiments are described herein as using a network 110 such as the Internet, other distribution techniques may be implemented that transmit information via memory cards, flash memory, or other portable memory devices.

Accordingly, the vision screening device 104 described herein may monitor the accommodation state of a patient in real-time and record refractive error(s), pupil size(s), and gaze angle(s) while a visual acuity test is being performed (e.g., in real-time), resulting in more accurate determinations of refractive error. The vision screening device 104 may generate output and/or recommendations based in part on the refractive error. This enables greater accessibility to vision screening exams and provides recommendations for patients 112 regarding potentially identified vision problems (e.g., such as hyperopia and/or presbyopia).

Figure 2:
FIG. 2 shows a schematic block diagram of components of a vision screening device used in the visual acuity screening environment of FIG. 1.
Figure 2:
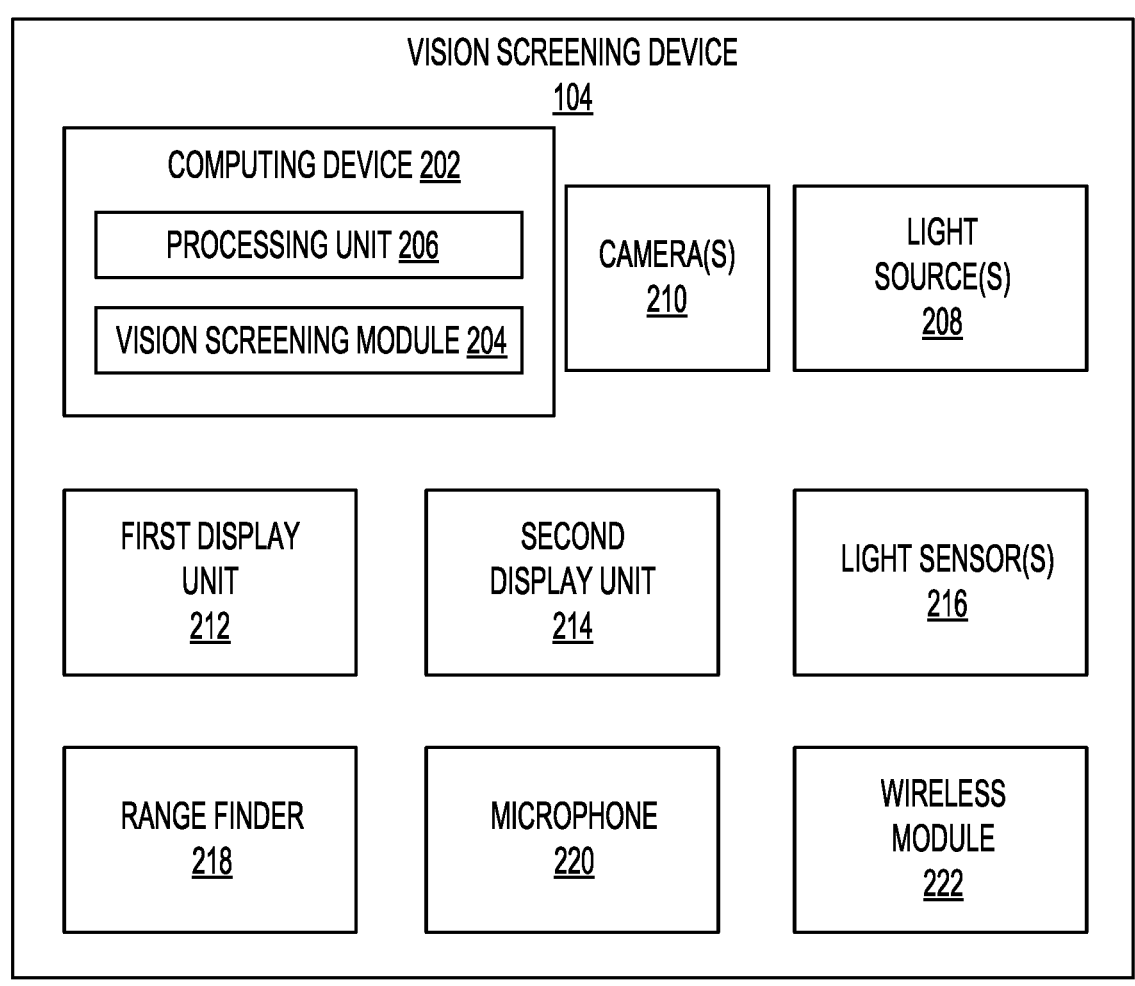

FIG. 2 is a schematic block diagram illustrating components of example vision screening device 104. As illustrated, example vision screening device 104 includes computing device 202, light source(s) 208, first display unit 212, second display unit 214, light sensor(s) 216, a range finder 218, a microphone 220, and a wireless module 222. In some examples, the vision screening device 104 comprises a housing (not shown), which provides support for components of vision screening device 104 as well as one or more aspects configured to facilitate hand-held operation. In some examples, one or more of the components of the vision screening device 104 are disposed within, partially disposed within, and/or are located on the housing.

Computing device 202 includes vision screening module 204 and processing unit 206. Vision screening module 204 comprises memory storing instructions for one or more of displaying a refractive error result and/or any other test result and/or data on the first display unit 212, processing images received on the light source(s) 208, and guiding and informing the user 102 about optotype display and test results for the patient 112. Optotypes include, for example, letters, shapes, objects, and numbers. In some examples, the vision screening module is included as part of the processing unit 206 described below.

Processing unit 206 comprises one or more processor(s), controller(s), at least one central processing unit ("CPU"), memory, and a system bus that couples the memory to the CPU. In some examples, the memory of the processing unit 206 includes system memory and mass storage device. System memory includes random access memory ("RAM") and read-only memory ("ROM"). In some examples, a basic input/output system (BIOS) that contains the basic routines that help to transfer information between elements within the example computing device 202, such as during startup, is stored in the ROM. In some examples, the mass storage device of the processing unit 206 stores software instructions and data. In some examples, mass storage device is connected to the CPU of the processing unit 206 through a mass storage controller (not shown) connected to the system bus. The processing unit 206 and its associated computer-readable data storage media provide non-volatile, non-transitory storage for the example computing device 202. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 202.

In some examples, the processing unit 206 of the computing device 202 communicates with the components of vision screening device 104, including light source(s) 208, camera(s) 210, first display unit 212, second display unit 214, light sensor(s) 216, range finder 218, microphone 220, and wireless module 222. In some examples, vision screening device further comprises a lens (not shown), which may be adjustable. In this example, the processing unit 206 communicates with a controller of a device, such as a mechanical motor, that is configured to receive instructions from the processing unit 206 and, based at least partly on executing the instructions, adjust the position of the lens or a focus setting of the lens.

In some examples, the processing unit 206 is configured to display one or more visual stimuli on the second display unit 214. In some examples, the processing unit 206 is configured to instruct the light source(s) 208 and/or cameras) 210 to capture image(s) of an eye of a patient. The processing unit 206 is further configured to process and/or analyze images received via the light source(s) 208 and/or camera(s) 210 and determine, based at least partly on the image(s), one or more of refractive error, pupil size, and/or gaze angle of the one or more eyes of a patient 112. In some examples, the processing unit 206 is further configured to determine and/or generate output and/or a recommendation for the patient. In some examples, the processing unit 206 is configured to display the output and/or recommendation on the first display unit 212. In some examples, the processing unit 206 processes and/or analyzes the image(s) using image processing techniques (e.g., positional analysis, object detection, etc.) and/or machine learning mechanisms.

Machine-learning mechanisms include, but are not limited to supervised learning algorithms (e.g., artificial neural networks, Bayesian statistics, support vector machines, decision trees, classifiers, k-nearest neighbor, etc.), unsupervised learning algorithms (e.g., artificial neural networks, association rule learning, hierarchical clustering, cluster analysis, etc.), semi-supervised learning algorithms, deep learning algorithms, etc.), statistical models, etc. In at least one example, machine-trained data models can be stored in memory associated with the computing device 202 and/or the server 106 for use during operation of the vision screening device 104.

Light source(s) 208 are configured to emit radiation (e.g., in the form of light) from the vision screening device 104 into an eye of a patient 112. In some examples, the light source(s) 208 comprise one or more light emitting diodes (LEDs), infrared (IR) LEDs, near IR LEDs, lasers (e.g., laser sensors), etc. In some examples, the light source(s) 208 comprise an LEI) array. In some examples, the LED array comprises visible LEDs, IR LEDs, and/or near-IR LEDs. In some examples, the near-IR LEDs in the LED array have a wavelength of about 850 nanometers (nm) and are used in capturing pupil images. Generally, the visible LEDs in the LED array have a wavelength of less than about 630 nm. This configuration allows for visual stimulus to be shown to the patient 112, but not seen in the images captured by the camera(s) 210 and/or light sensors) 216 described below. In some embodiments, the visible LEDs and/or IR LEDs are positioned between, and co-planar with, the near-IR LEDs in the LED array.

As illustrated, vision screening device 104 comprises one or more cameras) 210. In some examples, the camera(s) 210 are configured to capture digital images of the patient's eye, retina, and/or cornea in response to receiving instructions from the processing unit 206 and/or sensing returned radiation (e.g., such as via light sensor(s) 216, described below). For instance, in some examples, the camera(s) 210 comprise an image sensor array, such as a complementary metal-oxide semiconductor (CMOS) sensor array, also known as an active pixel sensor (APS), or a charge coupled device (CCD) sensor. In some examples, the camera(s) 210 comprise a lens that is supported by the vision screening device 104 and positioned in front of the light sensor array. The digital images are captured in various formats, such as PEG, BITMAP, TIFF, PGM, PGV, etc. In some examples, the camera(s) 210 are configured to have a plurality of rows of pixels and a plurality of columns of pixels. In some embodiments, the camera(s) 210 comprise about 1280 by 1024 pixels, about 640 by 480 pixels, about 1500 by 1152 pixels, about 2048 by 1536 pixels, or about 2560 by 1920 pixels. In some examples, the camera(s) 210 are configured to capture about 25 frames per second (fps); about 30 fps; about 35 fps; about 40 fps; about 50 fps; about 75 fps; about 100 fps; about 150 fps; about 200 fps; about 225 fps; or about 250 fps. It is understood that the above pixel counts are merely examples, and in additional embodiments the light source(s) 208 may have a plurality of rows including greater than or less than the number of pixels noted above.

First display unit 212 conveys information to user 102 about the positioning of the vision screening device 104, including test results, recommendation(s), and/or prescription(s). In some examples, the first display unit 212 is positioned on a first end of the housing of the vision screening device 104, such that first display unit 212 faces the patient 112 during typical operation. In some examples, the first display unit 212 comprises a liquid crystal display (LCD) or active matrix organic light emitting display (AMOLED). In some examples, the first display unit 212 is touch-sensitive and configured to receive input from the user 102. Information provided to the user 102 via first display unit 212 comprises the patient's 112 distance (e.g., such as distance d1 described in FIG. 1 above) from the vision screening device 104, a quality of the focus, progress of the evaluation, results of the evaluation, recommendations, prescription(s), and/or options for transmitting the results to another database (e.g., such as database 108 or any other database), via network 110.

Second display unit 214 displays one or more visual tests and/or visual stimuli to the patient 112. In one implementation, second display unit 214 is a display, such as a liquid crystal display (LCD) or an active matrix organic light emitting display (AMOLED). As described above, the second display unit 214 communicates with computing device 202, via processing unit 206. In some examples, the second display unit 214 comprises one or more of the light source(s) 208 described above, such as a light-emitting diode (LED)

array having visible LEDs, IR LEDs, and/or near-IR LEDs. In some examples, second display unit 214 is positioned on an opposite end of the housing of the vision screening device 104, relative to the first display unit 212, such that second display unit 214 faces the patient 112 during typical operation. In some examples, the second display unit 214 includes a display and one or more light source(s) 208 (e.g., LEDs or LED arrays). In some examples, the second display unit 214 comprises one or more of the light source(s) 208 described above, such as a light-emitting diode (LED) array having visible LEDs, IR LEDs, and/or near-IR LEDs. In some examples, the second display unit 214 comprises one or more amber LEDs in an LED array. Amber LEDs have a wavelength of about 608 nm to about 628 nm. The processing unit 206 regulates the amount of power directed to the LEDs in the LED array. For instance, in order to minimize the patient's 112 pupil constriction and eye strain, the processing unit 206 instructs the second display unit 214 to emit radiation from the amber LEDs at low to medium power. For example, a 20 mA LED can be run at between about 2 mA to about 10 mA. Alternatively, low brightness amber LEDs can be used, for example, LEDs that run at about 0.5 mA. Additionally, LEDs can be pulse modulated. Visible light LEDs in colors other than amber, when present in the second display unit 214, can also be operated at low to medium power. Further, in some examples the vision screening device 104 may include one or more diffusers disposed in an optical path of one or more LEDs in the LED array. For example, such a diffuser may comprise a window, lens, prism, filter, and/or other substantially transparent optical component configured to at least partly diffuse radiation emitted by the one or more LEDs. As a result, for example, light emitted (e.g., as radiation) from the light source(s) 208 (e.g., by the one or more LEDs) of the second display unit 214 may not appear to be as sharply defined when observed by the patient 112. In some such examples, diffusing light emitted by one or more of the LEDs in this way may reduce an amount of accommodation by the patient 112 and, as a result, the improve the accuracy of the refractive error measurement made by the vision screening device 104.

Light sensor(s) 216 of the vision screening device 104 comprise one or more sensor(s) configured receive light and conveys image data to processing unit 206 of computing device 202. In some examples, the light sensor(s) 216 comprise an image sensor array, such as a complementary metal-oxide semiconductor (CMOS) sensor array, also known as an active pixel sensor (APS), or a charge coupled device (CCD) sensor. In some examples, the light sensor(s) 216 may comprise one or more ambient light sensor(s) (not shown) that may receive ambient light information and conveys the ambient light information to the processing unit 206 of computing device 202. In some examples, the processing unit 206 may utilize the ambient light information in order to more accurately interpret pupil size data (e.g., are pupil size(s) of a patient within a normal range for level of detected ambient light?, etc.).

In some examples, a lens is supported by the vision screening device 104 and positioned in front of the light sensor(s) 216. For instance, in some examples, the light sensor(s) 216 are included as part of the camera(s) 210 described above. As noted above, in some examples, the light sensor(s) 216 are positioned on the interior of (e.g., disposed within) the housing of the vision screening device 104 and behind the second display unit 214, or adjacent thereto. Alternatively, the light sensor(s) 216 are positioned adjacent to second display unit 214 (e.g., below or above the second display unit 214) such that returned radiation need not pass through second display unit 214 to reach the light sensor(s) 216. Based at least in part on the returned radiation detected and/or sensed by the light sensor(s) 216, the camera(s) 210 capture one or more images of the eye, retina and/or cornea of the patient 112. In still further examples, the second display unit 214 may be disposed orthogonal to the light sensor(s) 216. In such examples, the second display unit 214 is configured to project an image onto a window, mirror, lens, or other substantially transparent substrate through which the light sensor(s) 216 detect the returned radiation.

In some examples, light sensor(s) 216 include photodiodes that have a light-receiving surface and have substantially uniform length and width. During exposure, the photodiodes convert the incident light to a charge. In some examples, the light sensor(s) 216 can be operated as a global shutter, that is, substantially all of the photodiodes are exposed simultaneously and for substantially identical lengths of time. Alternatively, the light sensor(s) 216 may be used with a rolling shutter mechanism, in which exposures move as a wave from one side of an image to the other. Other mechanisms are possible to operate the light sensor( ) 216 in yet other embodiments. In some examples, light sensor(s) 216 are capable of capturing digital images in response to receiving instructions from the processing unit 206. The digital images can be captured in various formats, such as JPEG, BITMAP, TIFF, PGM, PGV, etc.

In some examples, the light source(s) 208 and/or other components of the vision screening device 104 may perform one or more of the same functions (either alone or in combination with the light sensor(s) 216) described above with respect to the light sensor(s) 216. In particular, in some examples the light source(s) 208 may capture an initial image of the ambient surroundings. The computing device 202 may then determine, based at least in part on the captured image, whether there is too much ambient or IR light to perform one or more of the photorefraction operations described herein. If so, the computing device 202 may control the second display unit 214 to instruct the user 102 or patient 112 to use a light block, or move to an environment with less ambient light.

For example, in some embodiments the light source(s) 208 and/or the vision screening device 104, generally, may be configured to tolerate up to a threshold level of ambient IR light. In such examples, too much IR light from incandescent bulbs or sunlight may cause pupil images to be over exposed and washed out. Too much ambient visible light, by contrast, may cause the pupils of the patient 112 to be too small to measure with accuracy. In such examples, the light source(s) 208 and/or the vision screening device 104, generally, may be configured to sense both ambient visible and IR light, and to inform the user 102 as to visible and IR light levels that may be above respective thresholds. In such examples, a photodiode could be used to sense the overall level of ambient light, and an image captured by the light source(s) 208 with all the IR LED's turned off could be used as a measure of ambient IR light.

In some examples, light sensor(s) 216 are configured to detect and/or sense information about the environment. For example, light sensor(s) 216 of vision screening device 104 may record the quantity of ambient light, time of day, ambient noise level, etc. This data can additionally be used to, for example, evaluate refractive error testing. In some examples, the computing device 202 may utilize the information about the environment (e.g., ambient light) of the patient with a pupil size of the patient to determine whether the pupil size is within a normal threshold (e.g., based on data stored in a database of the system).

In some examples, light sensor(s) 216 detect the ambient light intensity around the vision screening device 104. Above certain brightness thresholds, the patient's 112 pupils constrict to the point where the diameter of the pupil is so small that the vision screening device 104 may not be configured to determine the refractive error of the patient 112 accurately. If computing device 202, in combination with light sensor(s) 216, determines the ambient light is too bright, second display unit 214 communicates to the user 102 or patient 112 to use a light block or move to an environment with less ambient light. In some examples, the computing device 202 may also be configured to adjust and/or otherwise control the brightness, sharpness, contrast, and/or other operational characteristic of the second display unit 214 based at least in part on one or more signals received from the light sensor(s) 216. For example, based at least in part on the ambient light intensity measured by the light sensor(s) 216, the computing device 202 may be configured to adjust (e.g., automatically, dynamically, and/or in real time) the brightness, backlight, and/or other parameters of the second display unit 214 in order to maintain the contrast ratio at a desired level or within a desired range.

In some examples, the light source(s) 208 and/or other components of the vision screening device 104 may perform one or more of the same functions (either alone or in combination with the light sensor(s) 216) described above with respect to the light sensor(s) 216. In particular, in some examples the light source(s) 208 may capture an initial image of the ambient surroundings. The processing unit 206 of the computing device 202 may then determine, based at least in part on the captured image, whether there is too much ambient or IR light to perform one or more of the photorefraction operations described herein. If so, the processing unit 206 may control the second display unit 214 to instruct the user 102 or patient 112 to use a light block, or move to an environment with less ambient light.

For example, in some embodiments the light source(s) 208 and/or the vision screening device 104, generally, may be configured to tolerate up to a threshold level of ambient IR light. In such examples, too much IR light from incandescent bulbs or sunlight may cause pupil images to be over exposed and washed out. Too much ambient visible light, by contrast, may cause the patient's 112 pupils to be too small to measure with accuracy. In such examples, the light source(s) 208 and/or the vision screening device 104, generally, may be configured to sense both ambient visible and IR light, and to inform the user 102 as to visible and IR light levels that may be above respective thresholds. In such examples, a photodiode could be used to sense the overall level of ambient light, and an image captured by the light source(s) 208 with all the IR LED's turned off could be used as a measure of ambient IR light.

Range finder 218, in combination with the processing unit 206 of the computing device 202, determines a distance (e.g., such as distance d1 described in FIG. 1 above) of the patient 112 from the vision screening device 104. In some examples, range finder 218 comprises an infrared transceiver unit, an ultrasonic transceiver unit, or another distance measuring unit known to one of skill in the art. Generally, the patient 112 is positioned about 1 meter (m), 10 feet, or 20 feet from the vision screening device 104. Other distances are possible, such as 16 inches, 20 inches, 30 inches, 35 inches, 40 inches, and 45 inches away. It is understood that the distances listed above are merely examples, and in additional embodiments, distances greater than or less than those noted above may be used during a visual acuity test and/or other tests described herein. As described above, the vision screening device 104 displays guidance to the patient 112 and/or the user 102 about how to adjust the relative positioning between the vision screening device 104 and the patient 112 to obtain a focal distance that will yield functional images. In embodiments where a user 102 operates the vision screening device 104, the guidance is displayed on first display unit 212. For example, first display unit 212 can display instructions to the user 102 indicating that the patient 112 is too close, too far away, or within a proper distance. In some embodiments, the focal length is about, 0.2 m, about 0.3 m, about 0.4 m, 0.5 m, about 0.6 m, about 0.7 m, about 0.75 m, about 0.8 m, about 0.9 m, about 1.0 m.

Microphone 220 senses audible sound and/or sound waved in inaudible frequencies. In some examples, the microphone 220 senses responses spoken by patient 112. In embodiments, the patient 112 speaks as part of the visual acuity test. For example, the patient 112 is asked to read an optotype, such as a letter, shown on the second display unit 214 and microphone 220 senses the patient's 112 responses. Then computing device 202, in combination with voice recognition software, decodes the responses and uses the decoded responses in the visual acuity determination. Additionally, or alternatively, the user 102 may record the patient's 112 responses manually and/or by interacting with one or more data input/touch input fields presented on the first display unit 212.

Wireless module 222 connects to external databases to receive and send refractive error and/or visual acuity test data using wireless connections. Wireless connections can include cellular network connections and connections made using protocols such as 802.11a, b, g, and/or ac. In other examples, a wireless connection can be accomplished directly between the vision screening device 104 and an external display using one or more wired or wireless protocols, such as Bluetooth, Wi-Fi Direct, radio-frequency identification (RFD), or Zigbee. Other configurations are possible. The communication of data to an external database can enable report printing or further assessment of the patient's 112 test data. For example, data collected and corresponding test results are wirelessly transmitted and stored in a remote database accessible by authorized medical professionals.

Moreover, as noted above, the cameras) 210 and/or light sensor(s) 216 capture one or more images of returned radiation from the patient's 112 pupils. The processing unit 206 of the computing device 202 and/or other components of the vision screening device 104 determine the patient's 112 refractive error. In some examples, the refractive error may be determined based at least partly on information related to the sphere, cylinder, axis, gaze angle 114, pupil diameter, inter-pupillary distance, ambient light level, and/or other characteristics of the patient 112. In some examples, the processing unit 206 and/or other components of the vision screening device 104 determine refractive error based at least in part on eccentric photorefraction methods and/or eccentric pupil refraction methods. The processing unit 206 of the computing device 202 and/or other components of the vision screening device 104 determine the patient's gaze angle and/or pupil size based at least partly on the image(s). In some examples and described in greater detail below, the computing device 202 and/or other components of the vision screening device 104 may utilize additional information in determining visual stimuli to display to the patient. In some examples, other characteristics (e.g., age, etc.) of the patient 112 are used to determine the visual stimuli. In some examples, the processing unit 206 and/or other components of the vision screening device 104 determine a recommendation for the patient 112 based at least partly on the refractive error and/or confidence metric.

Accordingly, the techniques herein enable a portable vision screening device to monitor accommodation state of a patient while a visual acuity test is being performed, resulting in more accurate determinations of refractive error. The portable vision screening device is further enabled to generate output and/or recommendations based in part on the refractive error. This enables greater accessibility to vision screening exams and provides recommendations for patients 112 regarding potentially identified vision problems (e.g., such as hyperopia and/or presbyopia).

Figures 3A, 3B:
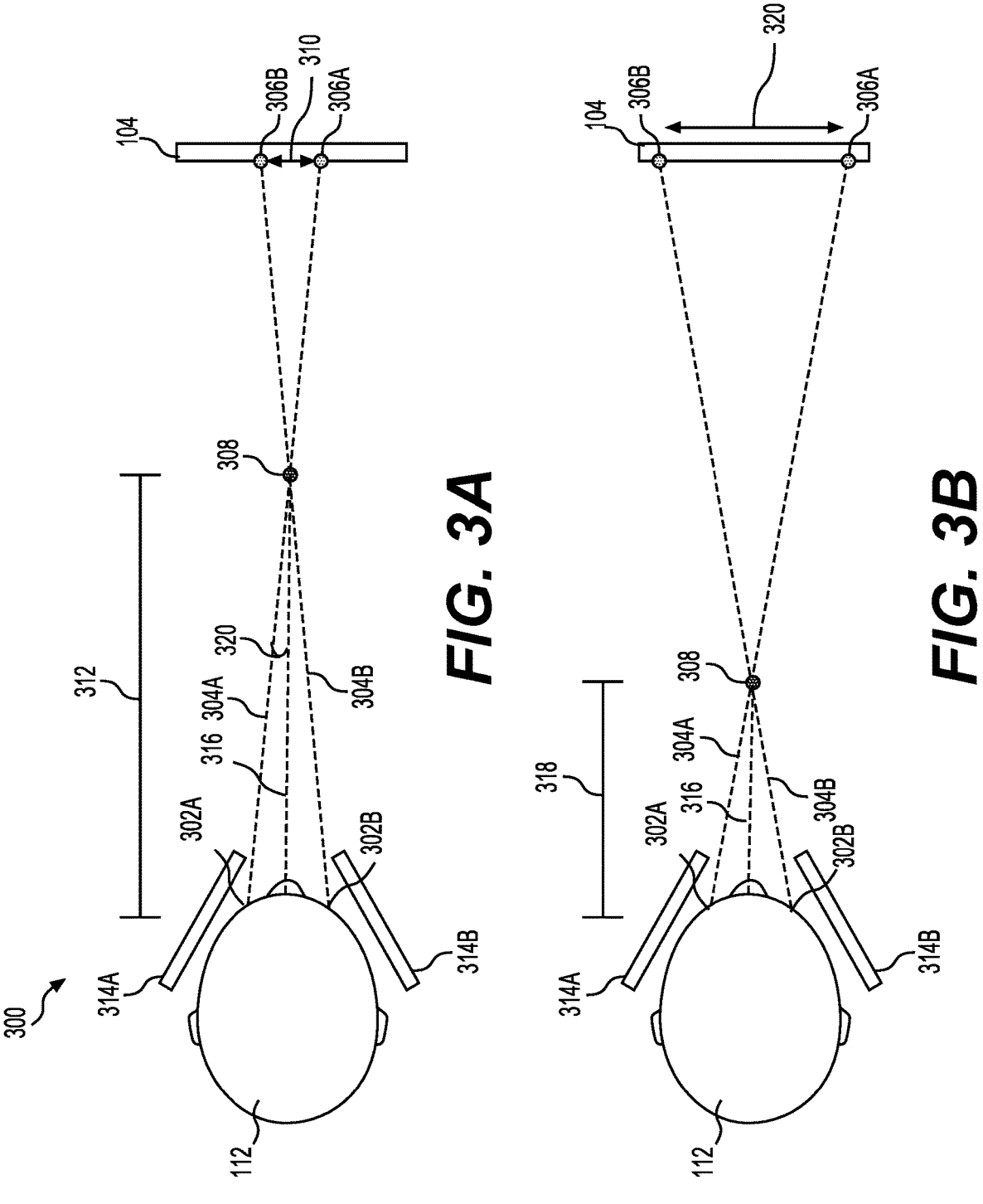
FIGS. 3A and 3B illustrate examples of how a vergence point of a patient may change when using the vision screening device of FIGS. 1 and 2.

FIGS. 3A and 3B illustrate examples of a system 300. In particular, FIGS. 3A and 3B illustrate how a vergence point of a patient may change when using the vision screening device described above. As illustrated in FIG. 3A, a patient 112 views visual stimuli 306A and 306B that is displayed on a screen of the vision screening device 104. In some examples, the screen corresponds to the second display unit 214, described above. The patient's left eye 302A views the visual stimuli 306A via the line of sight 304A for the left eye 302A. The right eye 302B of the patient 112 views the visual stimuli 306B via the line of sight 304B.

As illustrated in FIG. 3A, in some examples, the system 300 may include occluders 314A and 314B. In some examples, the occluders 314A, 314B comprise any tool (e.g., any plastic, metal, opaque material, or other material, that is held by the patient, worn by the patient, etc.) or other component of the system 300 configured to block light and/or portion(s) of light.

As illustrated in FIG. 3A, the occluder 314A blocks the light and/or portion(s) of the light to enable the left eye 302A of the patient 112 to focus on the visual stimuli 306A. Occluder 314B blocks the light and/or portion(s) of the light to enable the right eye 302B of the patient 112 to focus on the visual stimuli 306B. In the example shown in FIG. 3A, the visual stimuli 306A and 306B are spaced apart from each other at a distance 310. As illustrated in FIG. 3A, the lines of sight 304A, 304B of the patient 112 cross at point 308 (e.g., vergence point 308), such that, the visual stimuli 306A and 306B appear to be located at a distance 312 from the patient 112. The vergence point 308 represents where the gaze angles between the two eyes 302 of the patient 112 meet. Gaze angle generally represents an angle 320 between the line of sight and a central plane 316 that passes through the vergence point 308. Accommodation indicates the amount of or degree of focusing performed by each eye 302. In the illustrative examples, the eyes 302 of the patient 112 "accommodate" to the visual stimuli 306A and 306B on the display of the vision screening device 104.

As illustrated in FIG. 3B, the distance 318 that the visual stimuli 306A and 306B appear to be located relative to the patient 112 (i.e., the location of the vergence point 308 relative to the patient 112) changes as the visual stimuli 306A and 306B are moved farther apart (e.g., as the distance 320 on the display of the vision screening device 104 is increased). As noted above, the eyes 302 of the patient 112 accommodate to the visual stimuli 306A and 306B that are displayed by the vision screening device 104. For instance, as the visual stimuli 306A and 306B are moved further apart, the vergence point 308 moves closer to the patient due to accommodation by the eyes 302. Accordingly, as the vergence point 308 is at a closer distance 318 relative to the patient 112, the gaze angles 320 between the two eyes 302 of the patient 112 relative to the central plane 316 are greater than the gaze angles 320 described above with respect to the distance 312 and corresponding vergence point 308 of FIG. 3A. Thus, as described in greater detail below, the vision screening device 104 is configured to change the location of the visual stimuli 306 displayed to a patient 112 during a visual acuity exam. In doing so, the vergence point 308 of the patient 112 will change, such that the vision screening device 104 may capture radiation reflected from the cornea, retina, and/or eye of the patient, generate image(s) of the returned radiation, and determine gaze angle 320, pupil size, and/or refractive error of the eye(s) 302 In some examples, the techniques described herein may eliminate the need for occluders 314A, 314B. In other examples, the techniques described herein may utilize occluders 314A, 314B. Moreover, by changing the type and/or location of the visual stimuli 306A, 306B displayed to a patient (and thereby changing the vergence point 308), the accommodation state of the patient 112 can be changed, such that refractive error can be determined in near real-time, without allowing the patient 112 to accommodate. This results in a more accurate determination of refractive error, such as in patients with hyperopia.

Accordingly, the vision screening device 104 may be configured to display visual stimuli to a patient during a visual acuity exam and monitor accommodation state of the patient while the visual stimuli are moving and/or changing. The processing unit 206 of the vision screening device 104 causes the capture of one or more images (e.g., radiation reflected from the cornea(s), retina(s), etc.) of the patient's eyes) while the visual stimuli move and/or change. The processing unit 206 of the vision screening device 104 determines refractive error(s), pupil size(s), and gaze angle(s) 320 while the visual stimuli are moving and/or changing. For instance, the processing unit 206 may determine gaze angle 320 based on radiation reflected from the cornea of the patient. The processing unit 206 may determine refractive error based on radiation reflected from the retina of the patient. In some examples, the measured refractive error may be updated using vision acuity data (e.g., comparing pupil size, gaze angle, ambient light level, etc.). For instance, in some examples, the processing unit 206 may determine that the refractive error of a patient did not change. In this example, the processing unit 206 may also determine, based on the vision acuity data, that the gaze angle correctly tracked the accommodation guiding visual display. Accordingly, the vision screening device 104 may conclude that the subject has little accommodative amplitude (e.g., the subject is presbyopic). In another example, the patient may be young and may have pupils too small for the ambient light level. In this example, the processing unit 206 may determine that the patient's gaze angles are following the display and that the refractive error is changing within normal threshold limits. Accordingly, the vision screening device 104 may conclude that the patient is using accommodation to focus on the screen display and, thus, may be hyperopic.

Accordingly, the processing unit 206 of the vision screening device 104 can determine with whether the refractive error of the patient indicates hyperopia and/or presbyopia and a confidence metric associated with the refractive error. The processing unit 206 of the vision screening device 104 outputs results (e.g., test results (e.g., refractive error(s), diopters, etc.)) and/or a recommendation to the first display unit 212 of the vision screening device 104.

Figure 4A:
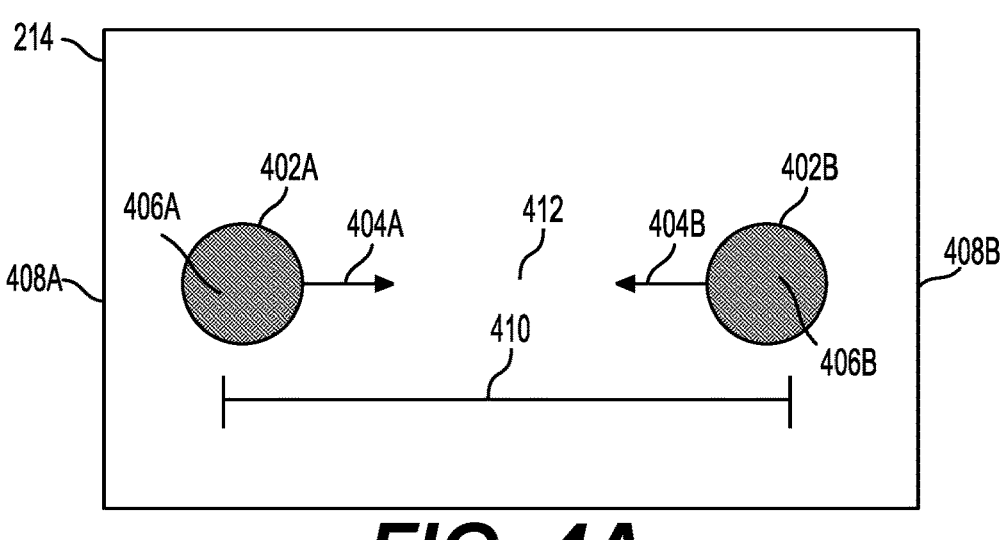
FIGS. 4A-4C illustrate examples of visual stimuli that the vision screening device described herein may display on the second display unit during a visual acuity exam.
Figure 4B:
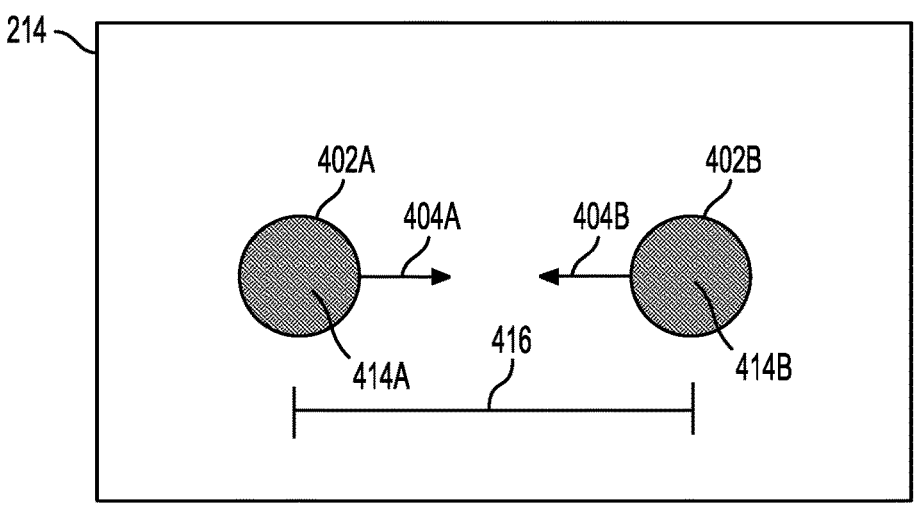
Figure 4C:
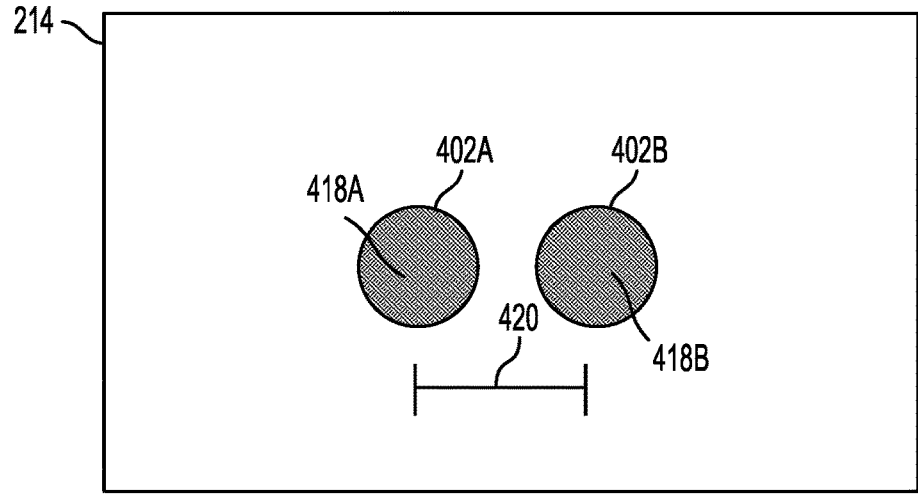

FIGS. 4A-4C illustrate examples of visual stimuli that the vision screening device 104 described above may display on the second display unit 214 during a visual acuity exam. While FIGS. 4A-4C illustrate an example of two visual stimuli, any suitable number of visual stimuli and/or visual stimuli type may be used (e.g., optotype(s), shape(s), image(s), pattern(s), etc.). In some examples, FIGS. 4A-4C correspond to visual stimuli that are displayed to a patient suspected of having hyperopia. For instance, in some examples, the second display unit 214 may display a single visual stimulus in the form of an optotype. In this example, the processing unit 206 of the vision screening device 104 captures image(s) of the patient's eye while the initial visual stimulus is displayed. The processing unit 206 processes and analyzes the image(s) and determines an initial refractive error. If the initial refractive error indicates that the patient may have hyperopia e.g., refractive error is above a threshold such that it indicates a hyperopia diagnosis associated with one or more eye(s)), the processing unit 206 may cause the second display unit 206 to display image(s) associated with determining hyperopia, such as images shown in FIGS. 4A-4C. In some examples, the images are displayed as a video, with the visual stimuli moving and/or changing in real-time, over a predetermined period of time (e.g., such as 5 seconds). In some examples, FIGS. 4A-4C are displayed upon receiving input, by the processing unit 206 of the vision screening device 104, indicating a selection of displaying images associated with determining hyperopia.

As shown in FIG. 4A, the second display unit 214 includes a first visual stimuli 402A and a second visual stimuli 402B (referred to as "visual stimuli" 402 herein). As illustrated, the first visual stimuli 402A is located at a position 406A on the second display unit 214 that is proximate to a first edge 408A of the second display unit 214. The second visual stimuli 402B is located at a second location 406B on the second display unit 214 that is proximate to a second edge 408B of the second display unit 214. The first visual stimuli 402A and the second visual stimuli 402B may be positioned at a first distance 410 apart. As noted above, the visual stimuli 402 may move and/or change over a period of time (e.g., such as 5 seconds). In the illustrated example, the visual stimuli 402 move and/or change in order to determine whether a patient has hyperopia. That is, the movement of the visual stimuli 402 on the second display unit 214 changes in order to invoke (e.g., encourage the patient to focus or otherwise accommodate to) far vision of the patient. In FIG. 4A, the first visual stimuli 402A moves in a first direction 404A towards the center 412 of the second display unit 214. The second visual stimuli 402B moves in a second direction 404B towards the center 412 of the second display unit 214.

As illustrated in FIG. 4B, the visual stimuli 402 are located at second respective locations 414A, 414B on the second display unit 214. As illustrated in FIG. 4B, the second respective locations 414A, 414B are located at a second distance 416 apart. The visual stimuli 402 may continue moving in directions 404A and 404B until the visual stimuli 402 reach respective end locations 418A, 418B, as illustrated in FIG. 4C. As noted above, the visual stimuli 402 may change while moving from the respective first locations 406A, 406B to the respective second locations 414A, 414B illustrated in FIG. 4B. For instance, the first visual stimuli 402A and/or the second visual stimuli 402B may change in shape (e.g., circle to square, triangle, rectangle, etc.), size, color, sharpness (e.g., blur), form (e.g., circle to optotype, circle to other image), and/or chromatic blur. In some examples, only a portion of the first visual stimuli 402A and/or the second visual stimuli 402B may change. As noted above, as the patient watches the visual stimuli 402 move and/or change from the first locations 406A, 406B illustrated in FIG. 4A to the second locations 414A, 414B illustrated in FIG. 4B, the processing unit 206 causes image(s) (e.g., such as visible light image(s), IR image(s), etc.) of the eyes of the patient to be captured in real-time. The processing unit 206 analyzes the image(s) and determines refractive error, pupil size, and gaze angle of the patient in real-time, such as which the image(s) are being displayed and/or changing. Accordingly, refractive error of the patient is determined in real-time (e.g., as the patient is encouraged to focus (e.g., accommodate) to far focus), such that the eyes are not accommodating, thereby resulting in a more accurate determination of refractive error.

In some examples, the processing unit 206 determines that there is a difference between the pupil size and/or gaze angle of the patient at the second locations 414 to the pupil size and/or gaze angle at the first locations 406. In some examples, the difference indicates that the patient is continuing to focus at the distance required by the test. For example, where the image(s) displayed correspond to a test for hyperopia, the first pupil size and first gaze angle recorded at the first locations 406 may indicate that the patient is focusing at a distance of 5 ft away from the vision screening device 104. As the visual stimuli 402 move to the respective second locations 414 illustrated in FIG. 4B, the recorded second gaze angle and second pupil size may indicate that the patient is focusing at a distance of 10 ft from the vision screening device 104. Based on this determination the processing unit 206 determines that the patient is continuing to invoke (e.g., encourage the patient to focus (e.g., accommodate) to) far focusing and proceeds to display FIG. 4C, as described below. However, if the processing unit 206 determines that the patient is not continuing to invoke far focusing (e.g., as indicated by the gaze angle and the pupil size), the processing unit 206 may pause the test, restart the test, and/or display different images to the patient in order to invoke far focus.

As illustrated in FIG. 4C, the visual stimuli 402 stop moving and/or changing after they reach the respective end locations 418A, 418B on the second display unit 214. In some examples, the respective end locations 418A, 418B may be preset based on one or more characteristics (e.g., size, resolution, etc.) of the second display unit 214 and/or the visual stimuli 402. In some examples, the respective end locations 418A, 418B may be a third distance 420 apart. In other examples, the respective end locations 418A, 418B may illustrate the visual stimuli 402 overlapping, or any other suitable illustration. As noted above, as the patient watches the visual stimuli 402 move and/or change from the second locations 414A, 414B illustrated in FIG. 4B to the end locations 418A, 418B illustrated in FIG. 4C, the processing unit 206 causes image(s) of the eyes of the patient to be captured in real-time. The processing unit 206 unit analyzes the image(s) and determines a final refractive error, final pupil size, and final gaze angle of the patient.

In some examples, the determination of refractive error may be reinforced using a confidence metric. The processing unit 206 determines the confidence metric based at least in part on the recorded final gaze angle and the final pupil size. For example, as described above, the processing unit 206 determines that there is a difference between the second pupil size and/or second gaze angle when the visual stimuli 402 are at the second locations 4141, 414B illustrated in FIG. 4B, to the final pupil size and/or final gaze angle when the visual stimuli 402 are at the end locations 418A, 418B illustrated in FIG. 4C. In some examples, the difference indicates that the patient is continuing to focus at the distance required by the test. For example, where the image(s) displayed correspond to a test for hyperopia, the second pupil size and second gaze angle recorded at the second locations 414A, 414B may indicate that the patient is focusing at a distance of 10 ft away from the vision screening device 104. As the visual stimuli 402 move to the respective end locations 418A, 418B illustrated in FIG. 4C, the recorded final gaze angle and final pupil size may indicate that the patient is focusing at a distance of 15 ft from the vision screening device 104. Accordingly, the processing unit 206 can determine a confidence metric (e.g., such as a mean error of one or more of: subject age, pupil size vs. ambient light, accommodation vs. display image, etc.) associated with the final refractive error, that indicates an accuracy associated with the final refractive error. That is, the confidence metric may indicate and/or confirm that the image(s) invoked far focusing of the patient, resulting in a more accurate determination of refractive error. In some examples, the processing unit 206 may utilize the confidence metric to provide a recommendation to a physician. For instance, a "high" confidence score or a "low" confidence may be associated with hyperopia and indicated to a physician. While the illustrative example describes the final refractive error, final pupil size, and final gaze as being recorded in association with an end image being displayed on the second display unit 214, such as when the patient is far focusing at 15 ft away (e.g., the visual stimuli 402 displayed on the second display unit 214 are close together and/or overlapping), it is understood that the final measurements may be recorded based on the processing unit 206 determining that the patient is focusing far enough away (e.g., in cases of a hyperopia test) and/or close enough (e.g., in cases of a presbyopia test) for the measurements to be valid.

Accordingly, the vision screening device 104 can display image(s) with changing visual stimuli. The patient may focus on the changing stimuli, thereby adjusting accommodation state of the patient and causing the vergence point to change. In this way, the vision screening device 104 determines refractive errors with improved accuracy, such that patients with hyperopia may be accurately identified. Additionally, by providing a confidence metric associated with the final refractive error, the vision screening device 104 is able to monitor the effectiveness and impact of vergence control on the patient's accommodation state.

In some examples, the visual stimuli 402 may move and/or change in different ways based at least in part on a test being performed. For instance, in some examples, the processing unit 206 of the vision screening device 104 receives input indicating an age of a patient. In some examples, the processing unit 206 of the vision screening device 104 can determine whether to run a test for presbyopia based at least in part on the age. In some examples, the processing unit 206 runs the test for presbyopia based on receiving input indicating a selection of the test for presbyopia. In this example, the processing unit 206 may display image(s) with the visual stimuli 402 starting at first locations similar to the locations 418A, 418B shown in FIG. 4C and moving the visual stimuli 402 to respective end locations similar to the locations 406A, 406B shown in FIG. 4A. As described above, the processing unit 206 may cause the visual stimuli 402 to change while moving over a predetermined time period. In this example, the relative motion of the visual stimuli 402 on the second display unit 214 influences the gaze angle (not shown) of the patient such that the patient accommodates to near focus (e.g., 40 centimeters, or any suitable distance for determining presbyopia). As described above, the processing unit 206 causes image(s) of the eyes of the patient to be captured while the visual stimuli 402 are moving and/or changing on the second display unit 214. In this example, as the visual stimuli 402 reach the respective end locations (e.g., such as the first locations 406A, 406B illustrated in FIG. 4A), a final refractive error, final pupil size, and/or final gaze angle is determined. The processing unit 206 determines whether there is a difference between the final refractive error and an expected refractive error. Based on the difference, the processing unit 206 outputs an indication of whether the patient has presbyopia (e.g., a diagnosis associated with presbyopia) to the first display unit 212, described in FIG. 2 above. Where the processing unit 206 determines a diagnosis of presbyopia exists (e.g., such as where there is a difference between the final refractive error and the expected refractive error), the output to the first display unit 212 may comprise a first refractive error associated with the patient's far vision, a second refractive error associated with the patient's near vision (e.g., determined by the presbyopia test), a confidence metric associated with the first and second refractive errors, and/or a recommendation. Accordingly, the vision screening device 104 determines recommendation for the patient based at least in part on refractive error(s) and confidence metric(s) of a patient's eye. For instance, where the processing unit 206 determines a diagnosis of presbyopia exists, the recommendation may include an indication that the patient 112 should follow up with an eye doctor. For instance, in examples where large groups are being evaluated (e.g., such as at a school), the processing unit 206 of the vision screening device 104 displays the recommendations via the first display unit 212.

FIGS. 5 and 6 illustrate example methods 500, 600 associated with the vision screening device 104 described above. The example methods 500, 600 of FIGS. 5 and 6, respectively, are illustrated as logical flow graphs, each operation of which represents a sequence of operations that may be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations may be combined in any order and/or in parallel to implement the processes. Although any of the processes or other features described with respect to the methods 500 and/or 600 may be performed by processor(s) and/or controller(s) of server 106, for ease of description, the example methods 500 and 600 will be described below as being performed by the processor(s) 206 (e.g., processing unit 206 described above) of the vision screening device 104 unless otherwise noted.

As illustrated in FIG. 5, at 502, a processing unit 206 of the vision screening device 104 causes a first image of a visual stimulus at a first location to be displayed (e.g., such as via the second display unit 214 of the vision screening device 104). In some examples, the first image comprises one or more visual stimuli, such as visual stimuli 402 described above. The visual stimulus displayed at 502 may comprise any suitable form (e.g., optotype(s), shape(s), image(s), pattern(s), etc.). In some examples, the first location corresponds to a starting location on the second display unit 214 (e.g., such as the first locations 406A and/or 406B described in FIG. 4A above). In some examples, the first image comprises a first visual stimulus that is displayed to help determine whether the patient has an indication of myopia or hyperopia. As noted above, the processing unit 206 causes the second display unit 214 to direct radiation (e.g., light radiation) towards an eye of a patient as the first image is displayed.

At 504, the processing unit 206 causes a first portion of reflected radiation to be captured. In some examples, the first portion of the reflected radiation comprises radiation that is reflected from the eye (e.g., cornea, retina, etc.) of the patient while the first image is being displayed. In some examples, the processing unit 206 causes the camera(s) 210 and/or light sensor(s) 208 to capture the first portion of the radiation. In some examples, the processing unit 206 generates an image based on the first portion of the radiation.

At 506, the processing unit 206 determines a first refractive error, a first gaze angle, and/or a first pupil size. In some examples, one or more of these determinations are made based at least in part on the first portion of radiation. For instance, as described above, the processing unit 206 analyzes the first portion of the radiation (e.g., the image) using various techniques (e.g., image processing techniques and/or machine learning mechanism(s)) to determine the refractive error, first pupil size, and first gaze angle. As described above, the processing unit 206 determines the first refractive error using eccentric photorefraction methods and/or eccentric pupil refraction methods.

At 508, the processing unit 206 causes second image(s) to be displayed. In some examples, the second image(s) illustrate movement of the visual stimulus to a second location (e.g., such as second location(s) 414 described in FIG. 4 above) on the second display unit 214. In some examples, the movement of the visual stimulus from the first location 406 to the second location 414 occurs over a period of time (e.g., such as 5 seconds). The period of time may be predetermined and based at least in part on the visual acuity test being performed. In some examples, the second image(s) comprise a portion of a plurality of images that correspond to a video. In some examples, the processing unit 206 causes the second image(s) to be displayed based at least in part on determining a hyperopia diagnosis associated with the patient. For instance, the first refractive error may indicate that the patient is suspected of having hyperopia (e.g., such as having a refractive error of any positive value (e.g., +1 diopters, +2 diopters, etc.)) in one or more eyes. Based at least in part on this indication, the processing unit 206 identifies a plurality of images such as a video), including the second image(s), associated with a visual acuity test for hyperopia and causes a portion of the plurality of images (e.g., the second image(s)) to be displayed on the second display unit 214. In some examples, the visual stimulus displayed in the second image(s) is a different visual stimulus from the first visual stimulus displayed in the first image(s). For instance, the visual stimulus in the second image(s) may correspond to a visual stimulus associated with and/or optimized for the visual acuity test being performed (e.g., such as determining hyperopia). In other examples, the visual stimulus in the second image(s) is the same as the visual stimulus in the first image(s).

As noted above, the second image(s) may illustrate a change in characteristic(s) of the visual stimulus as the visual stimulus moves from a first location 406 on the second display unit 214 to a second location 414 on the second display unit 214. The characteristic(s) comprise one or more of a size, a shape, a form, a sharpness, a color, or a chromatic blur. In some examples, the processing unit 206 causes the characteristic of the visual stimulus to change while the second image(s) are displayed. In some examples, such as where multiple visual stimuli are displayed, characteristic(s) of one or more of the multiple visual stimuli can change during display of the second image(s). For instance, where the visual stimuli correspond to visual stimuli 402 described in FIGS. 4A-4C above, characteristic(s) of the first visual stimuli 402A may change during display of the second image(s) and characteristic(s) of the second visual stimuli 402B remain the same. In other instances, characteristic(s) of both the first visual stimuli 402A and the second visual stimuli 402B may change while the second image(s) are displayed. In some examples, characteristic(s) of the visual stimuli 402 may change in a same way (e.g., such as where both the first visual stimuli 402B and the second visual stimuli 402B change from circles to triangles of the same size) or in different way (e.g., such as where the first visual stimuli 402 exhibits chromatic blur that is red and the second visual stimuli exhibits chromatic blur that is blue).

At 510, the processing unit 206 causes a second portion of the reflected radiation be captured. In some examples, the processing unit 206 causes the camera(s) 210 and/or light sensor(s) 208 to capture the second portion of the radiation. In some examples, the processing unit 206 generates an image based on the second portion of the radiation.

At 512, the processing unit 206 determines a second refractive error, a second gaze angle, and/or a second pupil size. In some examples, this determination is made based at least in part on the second portion of the radiation (e.g., the image). For instance, as described above, the processing unit 206 analyzes the second portion of the radiation (e.g., the image) using various techniques (e.g., image processing techniques and/or machine learning mechanism(s)) to determine the second refractive error, second pupil size, and second gaze angle. As described above, the processing unit 206 determines the second refractive error using eccentric photorefraction methods and/or eccentric pupil refraction methods.

As described above, in some examples, the processing unit 206 determines that there is a difference between the second pupil size and/or second gaze angle and the first pupil size and/or first gaze angle. In some examples, the difference indicates that the patient is continuing to focus at the distance required by the visual acuity test. Based on this determination the processing unit 206 can determines that the patient is continuing to invoke far focusing and proceeds to step 514 below. However, if the processing unit 206 determines that the patient is not continuing to invoke far focusing (e.g., as indicated by difference), the processing unit 206 may pause the visual acuity test, restart the visual acuity test, and/or display different images to the patient in order to invoke far focus. Accordingly, by recording refractive error, pupil size, and gaze angle in real-time (e.g., while the second image(s) are being displayed), the processing unit 206 can confirm the accommodation state of the patient.

At 514, the processing unit 206 causes third image(s) to be displayed. In some examples, the third image(s) illustrate movement of the visual stimulus to a third location to be displayed. In some examples, the third image(s) comprise a second portion of the plurality of images that correspond to the video. In some examples, the third location corresponds to an end location 418A and/or 418B described in FIG. 4C above. As noted above, the third image(s) may illustrate a change in a characteristic of the visual stimulus as the visual stimulus moves from the second location 414 to the third location 418, the characteristic comprising one or more of a size, a shape, a form, a sharpness, a color, or a chromatic blur. In some examples, the processing unit 206 causes the characteristic of the visual stimulus to change while the third image(s) are displayed. In some examples, such as where multiple visual stimuli are displayed, characteristic(s) of one or more of the multiple visual stimuli can change during display of the third image(s). For instance, where the visual stimuli correspond to visual stimuli 402 described in FIGS. 4A-4C above, a characteristic of the first visual stimuli 402A may change during display of the third image(s) and characteristic(s) of the second visual stimuli 402B remain the same. In other instances, characteristic(s) of both the first visual stimuli 402A and the second visual stimuli 402B may change while the third image(s) are displayed. In some examples, characteristic(s) of the visual stimuli 402 may change in a same way (e.g., such as where both the first visual stimuli 402B and the second visual stimuli 402B change from circles to triangles of the same size) or in different way (e.g., such as where the first visual stimuli 402 exhibits chromatic blur that is red and the second visual stimuli exhibits chromatic blur that is blue).

At 516, the processing unit 206 causes a third portion of the reflected radiation to be captured. In some examples, the third portion of the reflected radiation is captured while the third image(s) are being displayed on the second display unit 214. In some examples, the processing unit 206 causes the camera(s) 210 and/or light sensor(s) 208 to capture the third portion of the radiation. In some examples, the processing unit 206 generates an image based on the third portion of the radiation. In some examples, the third location 418 corresponds to end location of the visual stimuli. As described above, the end location may be preset based on one or more characteristics (e.g., size, resolution, etc.) of the second display unit 214 and/or the visual stimulus.

At 518, the processing unit 206 determines a final refractive error, a final gaze angle, and/or a final pupil size. In some examples, this determination is made based at least in part on the third portion of the radiation (e.g., the image) and/or determining that the third location 418 corresponds to the end location. For instance, as described above, the processing unit 206 analyzes the third portion of the radiation (e.g., the image) using various techniques (e.g., image processing techniques and/or machine learning mechanism(s)) to determine the final refractive error, final pupil size, and final gaze angle. As described above, the processing unit 206 determines the final refractive error using eccentric photorefraction methods and/or eccentric pupil refraction methods.

At 520, the processing unit 206 outputs results to the first display unit. In some examples, the results comprise test results associated with the visual acuity exam (e.g., final refractive error, final gaze angle, and/or final pupil size) and/or a confidence metric associated with the final refractive error. As described above, the processing unit 206 determines the confidence metric based at least in part on the final gaze angle and final pupil size. For instance, processing unit 206 determines, based at least in part on the first gaze angle and/or second gaze angle, whether the final gaze angle indicates that the patient's gaze has shifted and/or changed more than a threshold amount, thereby indicating the gaze angle indicates that the patient exhibits far focus. In some examples, the results further comprise a recommendation associated with the patient. For instance, the recommendation may indicate whether a follow-up consultation is needed. In some examples, the results may comprise an indication that the patient has hyperopia (e.g., such as an indicator of diopters), and/or a hyperopia diagnosis associated with the patient. In some examples, the processing unit 206 causes the results and/or recommendation to be displayed on a display of the vision screening device 104, such as via the first display unit 212. In some examples, the processing unit 206 sends the results and/or recommendation to a computing device via a network 110, for display on the computing device. In some examples, the processing unit 206 sends information associated with the patient to a remote server, the information including the results and/or recommendation.

Accordingly, the techniques described herein monitor accommodation state of a patient in real-time and record refractive error(s), ambient light level(s), pupil size(s), and gaze angle(s) while a visual acuity test is being performed (e.g., in real-time), resulting in more accurate determinations of refractive error and more accurate identification of patients with hyperopia (e.g., such as children). Additionally, the techniques described herein generate output and/or recommendations based in part on the refractive error. This enables greater accessibility to vision screening exams and provides recommendations for patients 112 regarding potentially identified vision problems (e.g., such as hyperopia).

FIG. 6 illustrates another example method 600 associated with the example vision screening device 104 described above. As illustrated in FIG. 6, at 602 a processing unit 206 receives input indicating an age of a patient. In some examples, the processing unit 206 receives the input via the first display unit 212, described in FIG. 2 above. In other examples, the processing unit 206 may receive the input via the second display unit 214, such as from the patient.

At 604, the processing unit 206 causes a visual stimulus at a first location (e.g., such as location(s) 418 described in FIG. 4C above) to be displayed (e.g., such as on the second display unit 214). In some examples, the processing unit causes the second display unit 214 to display a first image of a plurality of images, where the first image includes the visual stimulus. In some examples, the first image includes a plurality of visual stimuli. In some examples, the visual stimulus comprises an image, optotype, shape, or any other suitable stimuli associated with testing for presbyopia. In some examples, the processing unit 206 causes the visual stimulus to be displayed in response to the input indicating the age of the patient. For instance, where the input indicates the patient is above a threshold age (e.g., such as older than 8 years old), the processing unit 206 may cause the first image to be displayed. In other examples, the processing unit 206 causes the first image to be displayed in response to receiving input, such as input from the user. For instance, the processing unit 206 may cause a selectable option to be displayed on the first display unit 212 that, upon selection, runs a visual acuity test for presbyopia. The processing unit 206 may receive input from the user that indicates selection of the visual acuity test for presbyopia and, in response to the input, cause the first image of the visual stimulus at the first location to be displayed on the second display unit 214. As noted above, the processing unit 206 causes the second display unit 214 to direct radiation (e.g., light radiation) towards an eye of a patient as the first image is displayed.

At 606, the processing unit 206 causes first image(s) to be captured. In some examples, the first image(s) are captured while the visual stimulus is displayed at the first location 418. In some examples, the first image(s) include a first portion of radiation reflected from the eye (e.g., cornea, retina, etc.) of the patient. In some examples, the processing unit 206 generates the first image(s) based on the first portion of the radiation. In some examples, the processing unit 206 causes the camera(s) 210 and/or light sensor's) 208 to capture the first image(s) and/or first portion of the radiation.

At 608, the processing unit 206 determines a first refractive error, a first pupil size, and/or first gaze angle. In some examples, this determination is made based at least in part on the first image(s). For instance, as described above, the processing unit 206 analyzes the first image(s) using various techniques (e.g., image processing techniques and/or machine learning mechanism(s)) to determine the first refractive error, first pupil size, and first gaze angle. As described above, the processing unit 206 determines the first refractive error using eccentric photorefraction methods and/or eccentric pupil refraction methods.

At 610, the processing unit 206 causes the visual stimulus to be displayed at a second location (e.g., such as second location(s) 414 and/or first location(s) 404 described in FIGS. 4A and 4B above). For instance, the processing unit 206 may display second image(s) of the plurality of images, where the second image(s) illustrate movement of the visual stimulus from a first location 418 on the second display unit 214 to the second location 404 and/or 414 on the second display unit 214.

As noted above, the second image(s) may illustrate a change in characteristic(s) of the visual stimulus as the visual stimulus moves from the first location 418 on the second display unit 214 to a second location 404 and/or 414 on the second display unit 214. The characteristic(s) comprise one or more of a size, a shape, a form, a sharpness, a color, or a chromatic blur. In some examples, the processing unit 206 causes the characteristic of the visual stimulus to change while the second image(s) are displayed. In some examples, such as where multiple visual stimuli are displayed, characteristic(s) of one or more of the multiple visual stimuli can change during display of the second image(s). For instance, where the visual stimuli correspond to visual stimuli 402 described in FIGS. 4A-4C above, characteristic(s) of the first visual stimuli 402A may change during display of the second image(s) and characteristic(s) of the second visual stimuli 402B remain the same. In other instances, characteristic(s) of both the first visual stimuli 402A and the second visual stimuli 402B may change while the second image(s) are displayed. In some examples, characteristic(s) of the visual stimuli 402 may change in a same way (e.g., such as where both the first visual stimuli 402B and the second visual stimuli 402B change from circles to triangles of the same size) or in different way (e.g., such as where the first visual stimuli 402 exhibits chromatic blur that is red and the second visual stimuli exhibits chromatic blur that is blue). In some examples, the second location 404 and/or 414 corresponds to an end location of the visual stimulus. As described above, the end location may be preset based on one or more characteristics (e.g., size, resolution, etc.) of the second display unit 214 and/or the visual stimulus.

At 612, the processing unit 206 causes second image(s) to be captured. For instance, the second image(s) may comprise a second portion of the reflected radiation. In some examples, first image(s) include a first portion of radiation reflected from the eye (e.g., cornea, retina, etc.) of the patient. In some examples, the processing unit 206 generates the second image(s) based on the second portion of the radiation. In some examples, the processing unit 206 causes the camera(s) 210 and/or light sensor(s) 208 to capture the second image(s) and/or second portion of the radiation.

At 614, the processing unit 206 determines a final refractive error, a final gaze angle, and/or a final pupil size. In some examples, this determination is made based at least in part on the second image(s) and/or determining the second location 404 and/or 414 corresponds to the end location. For instance, as described above, the processing unit 206 analyzes the second image(s) using various techniques (e.g., image processing techniques and/or machine learning mechanism(s)) to determine refractive error, pupil size, and gaze angle. As described above, the processing unit 206 determines refractive error using eccentric photorefraction methods and/or eccentric pupil refraction methods. In some examples, the final refractive error, final gaze angle, and/or final pupil size At 616, the processing unit 206 determines a difference between the final refractive error and an expected refractive error. In some examples, the expected refractive error comprises a refractive error corresponds to the first refractive error. In some examples, the processing unit 206 determines, based at least in part on the difference whether the patient requires additional correction (e.g., such as reading glasses, progressive lenses, etc.).

At 618, the processing unit 206 outputs results (e.g. such as to the first display unit 212). In some examples, the results comprise test results associated with the visual acuity exam (e.g., final refractive error, final gaze angle, and/or final pupil size) and/or a confidence metric associated with the final refractive error. As described above, the processing unit 206 determines the confidence metric based at least in part on the final gaze angle and final pupil size. For instance, processing unit 206 determines, based at least in part on the first gaze angle and/or second gaze angle, whether the final gaze angle indicates that the patient's gaze has shifted and/or changed more than a threshold amount, thereby indicating the gaze angle indicates that the patient exhibits near focus. In some examples, the results further comprise a recommendation associated with the patient. For instance, the results may comprise a presbyopia diagnosis associated with the eyes of the patient (e.g., such as an indicator of diopters), and may indicate whether a follow-up consultation is needed. In some examples, the processing unit 206 causes the results and/or recommendation to be displayed on a display of the vision screening device 104, such as via the first display unit 212. In some examples, the processing unit 206 sends the output and/or recommendation to a computing device via a network 110, for display on the computing device. In some examples, the processing unit 206 sends information associated with the patient to a remote server, the information including the results and/or recommendation.

Accordingly, the techniques described herein may monitor accommodation state of a patient in real-time and record refractive error(s), pupil size(s), and gaze angle(s) while a visual acuity test is being performed (e.g., in real-time), resulting in more accurate determinations of refractive error and more accurate identification of patients with presbyopia. Additionally, the techniques described herein generate output and/or recommendations based in part on the refractive error. This enables greater accessibility to vision screening exams and provides recommendations for patients 112 regarding potentially identified vision problems (e.g., such as presbyopia).

As noted above, the example devices and systems of the present disclosure may be used to perform vision screening tests. For example, components described herein may be configured to display, to a patient, a plurality of images that includes a visual stimulus, where the plurality of images illustrate movement of the visual stimulus over a period of time, utilize light sensor(s) to capture portion(s) of reflected radiation at different times during the period of time, determine refractive error(s), pupil size(s), and gaze angle(s), and display a recommendation.

As a result, the devices and systems described herein may assist a user in monitoring accommodation of a patient during a visual acuity exam and determining refractive error in hyperopic patients with improved accuracy, thereby streamlining vision screening exams. Moreover, the devices and systems described herein may assist a user with identifying hyperopic patients and/or patients with presbyopia and determining recommendations associated with eh patients (e.g., such as whether a follow-up is needed, reading glasses are needed, progressive lenses are needed etc.), thereby providing an integrated vision screening exam and enabling patients to receive care as early as possible (e.g., such as in the case of hyperopic children). This may streamline workflow for providing prescriptions, follow-up recommendations, and/or referrals for primary care physicians and others, thereby reduce the cost of treatments.

The foregoing is merely illustrative of the principles of this disclosure and various modifications can be made by those skilled in the art without departing from the scope of this disclosure. The above described examples are presented for purposes of illustration and not of limitation. The present disclosure also can take many forms other than those explicitly described herein. Accordingly, it is emphasized that this disclosure is not limited to the explicitly disclosed methods, systems, devices, and apparatuses, but is intended to include variations to and modifications thereof, which are within the spirit of the following claims.

As a further example, variations of apparatus or process limitations (e.g., dimensions, configurations, components, process step order, etc.) can be made to further optimize the provided structures, devices, and methods, as shown and described herein. In any event, the structures and devices, as well as the associated methods, described herein have many applications. Therefore, the disclosed subject matter should not be limited to any single example described herein, but rather should be construed in breadth and scope in accordance with the appended claims.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

The description and illustration of one or more embodiments provided in this application are not intended to limit or restrict the scope of the invention as claimed in any way. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A system, comprising:
a processing unit;
a light sensor operatively connected to the processing unit; and
non-transitory computer-readable media storing instructions that, when executed by the processing unit, cause the processing unit to perform operations comprising:

causing a first image including a visual stimulus to be displayed on a first display unit operatively connected to the processing unit, the first display unit directing radiation to an eye of a patient;

causing a first portion of the radiation reflected from the eye to be captured by the light sensor and during display of the first image;

determining, based at least in part on the first portion of the radiation, a first refractive error;

causing a plurality of second images including the visual stimulus to be displayed on the first display unit, the plurality of second images illustrating movement of the visual stimulus, from a first location on the first display unit to a second location on the first display unit, wherein the processing unit selects movement of the visual stimulus, from the first location to the second location, based on the first refractive error;

causing, during display of the plurality of second images, a second portion of the radiation reflected from the eye of the patient to be captured by the light sensor while the visual stimulus moves from the first location to the second location;

determining, based at least in part on the second portion of the radiation, a second refractive error; and causing a recommendation to be displayed on a second display unit operatively connected to the processing unit.

2. The system of claim 1, the operations further comprising:

determining, based at least in part on the first portion of the radiation, a first pupil size, a first ambient light level, and a first gaze angle;

determining, based at least in part on the second portion of the radiation, a second pupil size, a second ambient light level, and a second gaze angle; and determining a confidence metric associated with the second refractive error based at least in part on one or more of the first pupil size, the first gaze angle, the first ambient light level, the second pupil size, the second ambient light level, or the second gaze angle.

3. The system of claim 2, wherein the confidence metric is displayed together with the recommendation on the second display unit.

4. The system of claim 1, wherein the plurality of second images further illustrates movement of the visual stimulus moving from the second location on the first display unit to a third location on the first display unit, the operations further comprising;

causing a third portion of the radiation reflected from the eye of the patient to be captured by the light sensor while the visual stimulus moves from the second location to the third location;

determining, based at least in part on the third portion of the radiation, a third refractive error;

determining, based at least in part on the third refractive error, a hyperopia diagnosis associated with the patient; and causing the recommendation to be displayed on the second display unit, the recommendation including an indication of the hyperopia diagnosis.

5. The system of claim 4, the operations further comprising:

determining, based at least in part on the third portion of the radiation, a pupil size and a gaze angle; and determining a confidence metric associated with the third refractive error based at least in part on the pupil size and the gaze angle, wherein the confidence metric is displayed together with the recommendation on the second display unit.

6. The system of claim 1, the operations further comprising:

determining, based at least in part on the first refractive error, a hyperopia diagnosis associated with the patient, wherein:

the movement is selected based at least in part on the hyperopia diagnosis, and the movement comprises movement of the visual stimulus in a direction toward a center of the display unit.

7. The system of claim 1, wherein the movement is selected by the processing unit to invoke an accommodation response by the patient that corresponds to an eye condition diagnosis associated with the first refractive error.

8. The system of claim 1, wherein the visual stimulus comprises a first visual stimuli, and a second visual displayed together with the first visual stimuli, the first visual stimuli being separate and spaced from the first visual stimuli, and the movement comprising decreasing a distance between the first visual stimuli and the second visual stimuli.

9. A vision screening device comprising:

a processing unit;

a housing;

a display unit supported by the housing and operatively connected to the processing unit;

a light sensor supported by the housing and operatively connected to the processing unit; and memory storing instructions that, when executed by the processing unit, cause the vision screening device to:

cause a first image including a visual stimulus to be displayed on the display unit, the display unit directing radiation to an eye of a patient;

cause, during display of the first image, a first portion of radiation reflected from the eye of the patient to be captured by the light sensor;

determine, based at least in part on the first image, a first refractive error;

cause a plurality of second images including the visual stimulus to be displayed on the display unit, the plurality of second images illustrating movement of the visual stimulus from a first location on the display unit to a second location on the display unit, wherein the processing unit selects movement of the visual stimulus, from the first location to the second location, based on the first refractive error;

cause a second portion of the radiation reflected from the eye of the patient to be captured by the light sensor while the visual stimulus moves from the first location to the second location; and determine, based at least in part on the second portion of the radiation, a second refractive error.

10. The vision screening device of claim 9, the memory further storing instructions that, when executed by the processing unit, cause the vision screening device to:

determine, based at least in part on the first refractive error, that there is an indication of a hyperopia diagnosis associated with the patient; and based at least in part on the indication of the hyperopia diagnosis, causing the plurality of second images to be displayed.

11. The vision screening device of claim 9, the memory further storing instructions that, when executed by the processing unit, cause the vision screening device to:

send to a remote server, information associated with the patient, the information including at least the first refractive error and the second refractive error.

12. The vision screening device of claim 9, wherein the plurality of second images further illustrates the visual stimulus moving from the second location on the display unit to a third location on the display unit, the memory further storing instructions that, when executed by the processing unit, cause the vision screening device to:

capture, by the light sensor, a third portion of the radiation reflected from the eye of the patient while the visual stimulus moves from the second location to the third location;

determine, based at least in part on the third portion of the radiation, a third refractive error, a pupil size, and a gaze angle;

determine, based at least in part on the third refractive error, a hyperopia diagnosis associated with the patient;

determine, based at least in part on the pupil size and the gaze angle, a confidence metric associated with the third refractive error; and display a recommendation on a second display unit of the vision screening device, the recommendation including an indication of the hyperopia diagnosis, and the recommendation being displayed with the confidence metric.

13. The vision screening device of claim 9, wherein the plurality of second images comprises a video.

14. The vision screening device of claim 9, wherein the plurality of second images further illustrate a change in a characteristic of the visual stimulus as the visual stimulus moves from the first location to the second location, the characteristic comprising one or more of a size, a shape, a sharpness, a color, a form, or a chromatic blur.

15. A method, comprising:

causing, by a processing unit, a first image including a visual stimulus to be displayed on a display unit, the display unit directing radiation to an eye of a patient;

causing, by the processing unit and during display of the first image, a first portion of radiation reflected from the eye of the patient to be captured by a light sensor;

determining, by the processing unit and based at least in part on the first image, a first refractive error;

causing, by the processing unit, a plurality of second images including the visual stimulus to be displayed on the display unit, the plurality of second images illustrating movement of the visual stimulus from a first location on the display unit to a second location on the display unit, wherein the processing unit selects movement of the visual stimulus, from the first location to the second location, based on the first refractive error;

causing, by the processing unit, a second portion of the radiation reflected from the eye of the patient to be captured by the light sensor while the visual stimulus moves from the first location to the second location; and determining, by the processing unit and based at least in part on the second portion of the radiation, a second refractive error.

16. The method of claim 15, further comprising:

prior to causing the first image to be displayed on the display unit, receiving, by the processing unit and via a second display unit, input indicating an age of the patient; and wherein the first image is based at least in part on the age of the patient.

17. The method of claim 15, further comprising:

determining, based at least in part on the first refractive error, that there is an indication of a hyperopia diagnosis associated with the patient; and based at least in part on the indication of the hyperopia diagnosis, causing the plurality of second images to be displayed.

18. The method of claim 15, wherein the plurality of second images further illustrate a change in a characteristic of the visual stimulus as the visual stimulus moves from the first location to the second location, the characteristic comprising one or more of a size, a shape, a sharpness, a color, a form, or a chromatic blur.

19. The method of claim 15, wherein the first image comprises a first visual stimulus and the plurality of second images comprise a second visual stimulus that is different from the first visual stimulus.

20. The method of claim 15, further comprising:

determining, based at least in part on the first portion of the radiation, a first pupil size and a first gaze angle;

determining, based at least in part on the second portion of the radiation, a second pupil size and a second gaze angle; and determining a confidence metric associated with the second refractive error based at least in part on one or more of the first pupil size, the first gaze angle, the second pupil size, or the second gaze angle.

* * * * *